US011815517B2

(12) United States Patent
Sahakian et al.

(10) Patent No.: US 11,815,517 B2
(45) Date of Patent: *Nov. 14, 2023

(54) ANTIBODIES TO 25-HYDROXYVITAMIN D2 AND D3

(71) Applicant: Siemens Healthcare Diagnostics Inc., Tarrytown, NY (US)

(72) Inventors: Niver Panosian Sahakian, Encino, CA (US); Bruce A. Campbell, Calabasas, CA (US); Spencer Hsiang-Hsi Lin, Walnut Creek, CA (US); James Vincent Freeman, Sandy Hook, CT (US); Qimu Liao, Alhambra, CA (US); Ramon A. Evangelista, Laguna Hills, CA (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 301 days.

This patent is subject to a terminal disclaimer.

(21) Appl. No.: 17/087,914

(22) Filed: Nov. 3, 2020

(65) Prior Publication Data

US 2021/0055314 A1 Feb. 25, 2021

Related U.S. Application Data

(60) Division of application No. 15/915,001, filed on Mar. 7, 2018, now Pat. No. 10,837,973, which is a continuation of application No. 14/335,686, filed on Jul. 18, 2014, now abandoned, which is a continuation of application No. 13/458,847, filed on Apr. 27, 2012, now Pat. No. 8,785,603.

(60) Provisional application No. 61/488,630, filed on May 20, 2011.

(51) Int. Cl.
*G01N 33/82* (2006.01)
*C07K 16/44* (2006.01)

(52) U.S. Cl.
CPC .............. *G01N 33/82* (2013.01); *C07K 16/44* (2013.01); *G01N 2800/02* (2013.01)

(58) Field of Classification Search
None
See application file for complete search history.

(56) References Cited

U.S. PATENT DOCUMENTS

| | | | |
|---|---|---|---|
| 4,456,553 | A | 6/1984 | Oshida et al. |
| 5,075,465 | A | 12/1991 | Nakagawa et al. |
| 5,093,519 | A | 3/1992 | Bouillon et al. |
| 5,786,347 | A | 7/1998 | Hesse et al. |
| 5,821,020 | A | 10/1998 | Hollis |
| 6,787,660 | B1 | 9/2004 | Armbruster et al. |
| 6,929,797 | B2 | 8/2005 | Mazess et al. |
| 7,087,395 | B1 | 8/2006 | Garrity et al. |
| 7,482,162 | B2 | 1/2009 | Laurie et al. |
| 8,785,603 | B2 | 7/2014 | Campbell et al. |
| 2002/0062009 | A1 | 5/2002 | Taylor |
| 2003/0008321 | A1 | 1/2003 | Fukui et al. |
| 2003/0119018 | A1 | 6/2003 | Omura et al. |
| 2006/0057564 | A1 | 3/2006 | Wang |
| 2007/0083334 | A1 | 4/2007 | Mintz et al. |
| 2008/0148432 | A1 | 6/2008 | Abad |
| 2009/0012268 | A1 | 1/2009 | Bergmann et al. |
| 2010/0028357 | A1 | 2/2010 | Matsubara et al. |
| 2010/0068725 | A1 | 3/2010 | Armbruster et al. |
| 2010/0266493 | A1 | 10/2010 | Banga et al. |
| 2010/0311955 | A1 | 12/2010 | Guo et al. |
| 2011/0092372 | A1 | 4/2011 | Almagro et al. |
| 2011/0097733 | A1 | 4/2011 | Anciaux et al. |
| 2011/0117086 | A1 | 5/2011 | Pannequin et al. |

FOREIGN PATENT DOCUMENTS

| | | |
|---|---|---|
| EP | 0092004 | 10/1983 |
| JP | 2009509992 | 3/2009 |
| WO | 2002046746 | 6/2002 |
| WO | 2007039194 | 4/2007 |
| WO | 2007039193 | 12/2007 |
| WO | 2007140962 | 12/2007 |

(Continued)

OTHER PUBLICATIONS

Bruce W Holils et al: "Improved Radioimmunoassay for Vitamin D and Its Use in Assessing Vitamin D Status", Clinical Chemistry, vol. 31, No. 11, Nov. 1, 1985 (Nov. 1, 1985), pp. 1815-1819.

Andrew M Wootton: "Improving the Measurement of 25-hydroxyvitamin D", Clin Biochem Rev, vol. 26, No. 1, Feb. 1, 2005 (Feb. 1, 2005), pp. 33-36.

European Search Report dated Mar. 18, 2015 (8 pages).

Casadevall, A. et al; "Immunoglobulin isotype influences affinity and specificity"; Proceedings of the national academy of sciences; vol. 109; No. 31; pp. 12272-12273; XP55047920; ISSN: 0027-8424; DOI: 10.1073/pnas.1209750109 / Jul. 31, 2012.

(Continued)

*Primary Examiner* — Sharon X Wen

(57) ABSTRACT

Provided herein are antigenic molecules that can be used to generate antibodies capable of binding to a vitamin D derivative, such as 25-hydroxyvitamin D2 and/or 25-hydroxyvitamin D3, or a 25-hydroxyvitamin D analog, such as a vitamin D-C22 immunogenic molecule or compound. Antibodies produced using these antigenic molecules, and related antigenic compounds, are also described. In addition, disclosed herein are methods for detecting vitamin D deficiency in a subject, methods for treating a subject suspected of having a vitamin D deficiency, methods for monitoring progression of vitamin D deficiency in a subject, and methods for monitoring treatment of vitamin D deficiency in a subject in need thereof. The methods involve the detection or quantification of 25-hydroxyvitamin D2 and D3. Also provided are methods and reagents for the detection or quantification of 25-hydroxyvitamin D2 and D3, methods for stabilizing vitamin D analogs, and methods for separating 25-hydroxyvitamin D2 and D3 from vitamin D binding protein in a biological sample.

10 Claims, 15 Drawing Sheets

Specification includes a Sequence Listing.

(56) References Cited

FOREIGN PATENT DOCUMENTS

| WO | 2010/019566 | 2/2010 |
|---|---|---|
| WO | 2011/051348 | 5/2011 |

OTHER PUBLICATIONS

Shaw, S-Y et al; "A spontaneous variant of an antidigoxin hybridoma antibody with increased affinity arieses from a heavy chain signal peptide mutation"; Molecular immunology; Pergamon GB; vol. 29; No. 4; pp. 525-529, (1992).

Clemens, Thomas et al., "A simple method for generation of antibodies with specificity for 1, 25-dihydroxyergocalciferol and 1, 25-dihydroxycholecalciferol.", Steroids, vol. 42.5, Nov. 1983, pp. 503-509.

Panka, D. J. et al; "Variable region framework differences result in decreased o increased affinity of variant anit-digoxin antibodies"; Proceedings national academy of sciences PNAS; National academy of sciences; vol. 85; No. 9; pp. 3080-3084; (1988).

International Search Report for PCT/US2012/038637 dated Nov. 9, 2012.

Lloyd et al; "Protein Engineering, Design & Selection"; 2009; vol. 22; No. 3; pp. 159-168.

Khan et al; "How I Treat Vitamin D Deficiency"; J. Oncol Pract. 2010 6(2); pp. 97-101.

Hollis BW, Kamerud JQ, Selvaag SR, Lorenz JD, Napoli JL. Determination of vitamin D status by radioimmunoassay with an 125I-labeled tracer. Clin Chem. Mar. 1993;39(3):529-33.

Wallace AM, Gibson S, de la Hunty A, Lamberg-Allardt C, Ashwell M. Measurement of 25-hydroxyvitamin D in the clinical laboratory: current procedures, performance characteristics and limitations. Steroids. Jul. 2010;75(7):477-88. doi: 10.1016/j.steroids.2010.02. 012. Epub Feb. 24, 2010.

Galfre, G., Howe, S., Milstein, C. et al. Antibodies to major histocompatibility antigens produced by hybrid cell lines. Nature 266, 550-552 (1977) (Abstract only).

Oi V.T., Herzenberg L.A. Immunoglobulin-producing hybrid cell lines. In: Mishell B.B., Shiigi S.M., editors. Selected Methods in Cellular Immunology. W.H. Freeman and Co; San Francisco, CA: 1980. p. 351.

Narasimha Swamy et al., Biochemical and preliminary crystallographic characterization of the vitamin D sterol- and Actin-binding by human vitamin D-binding protein,Archives of Biochemistry and Biophysics, vol. 402, Issue 1, (2002,) pp. 14-23.

Fig. 1(a)
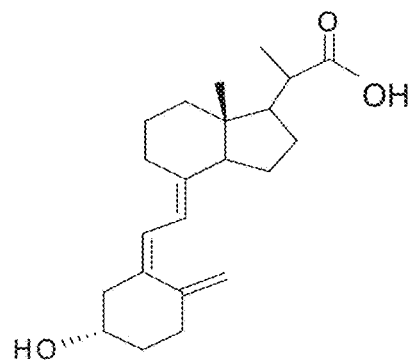
Fig. 1(b)
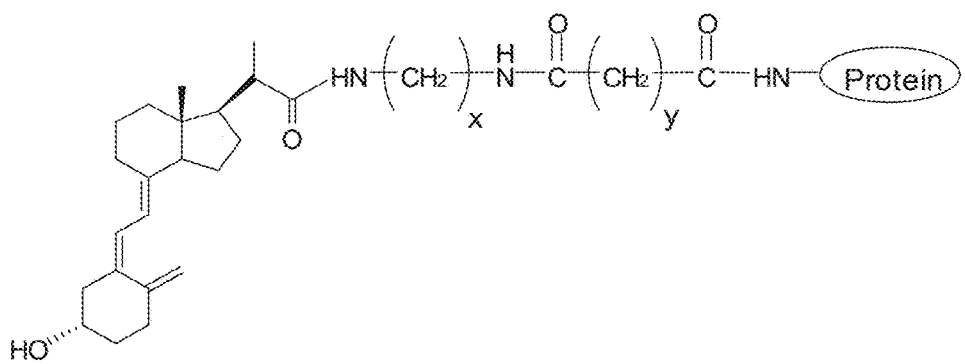
Fig. 1(c)
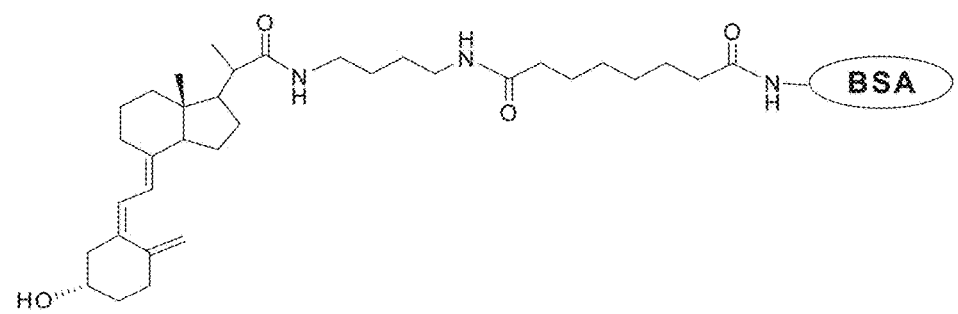
Fig. 1(d)
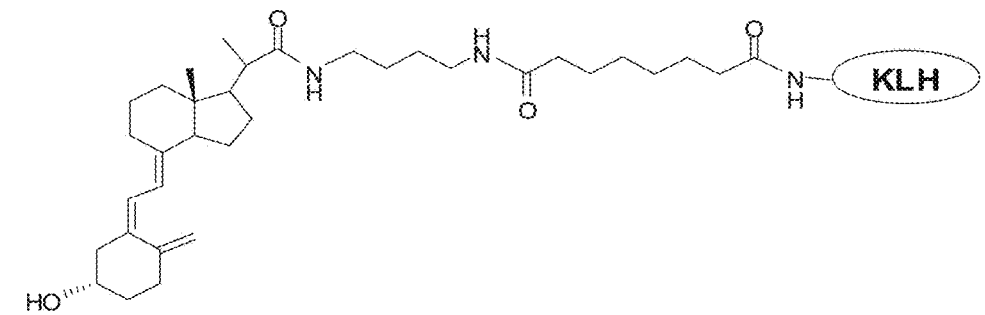
Figure 1

SEQUENCE LISTING

<160> NUMBER OF SEQ ID NOS: 36

<210> SEQ ID NO 1
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ttttggggcc aaggcaccac tctcacagtc tcctcg                             36

<210> SEQ ID NO 2
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tacaccatga actgggtgaa gcagagccat ggaaagaac                          39

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
tttactatct ataatcagaa g                                             21

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
ataagagcgc attacgacgg gagagtt                                       27

<210> SEQ ID NO 5
<211> LENGTH: 90

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gtgcagctgc tcgagtctgg acctgagctg gtgaagcctg gagcttcaat gaagatatcc    60
tgcaaggctt ctggttactc attcactgac                                    90

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
cttgagtgga ttggacttat taatccttac aatggt                             36

<210> SEQ ID NO 7
<211> LENGTH: 99
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
ttcaagggca aggccacatt aactgtagac aagtcatcca gcacagccta catggaactc    60
ctcagtctga catctgaaga ctctgcagtc tattacttt                          99

<210> SEQ ID NO 8
<211> LENGTH: 348
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
gtgcagctgc tcgagtctgg acctgagctg gtgaagcctg gagcttcaat gaagatatcc    60
tgcaaggctt ctggttactc attcactgac tacaccatga actgggtgaa gcagagccat   120
ggaaagaacc ttgagtggat tggacttatt aatccttaca atggttttac tatctataat   180
cagaagttca gggcaaggc cacattaact gtagacaagt catccagcac agcctacatg    240
gaactcctca gtctgacatc tgaagactct gcagtctatt actttataag agcgcattac   300
gacgggagag tttttgggg ccaaggcacc actctcacag tctcctcg                 348

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Phe Trp Gly Gln Gly Thr Thr Leu Thr Val Ser Ser
1               5                   10

<210> SEQ ID NO 10
```

-continued

```
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Tyr Thr Met Asn Trp Val Lys Gln Ser His Gly Lys Asn
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Phe Thr Ile Tyr Asn Gln Lys
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Ile Arg Ala His Tyr Asp Gly Arg Val
1               5

<210> SEQ ID NO 13
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Val Gln Leu Leu Glu Ser Gly Pro Glu Leu Val Lys Pro Gly Ala Ser
1               5                   10                  15

Met Lys Ile Ser Cys Lys Ala Ser Gly Tyr Ser Phe Thr Asp
            20                  25                  30

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Glu Trp Ile Gly Leu Ile Asn Pro Tyr Asn Gly
1               5                   10

<210> SEQ ID NO 15
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 15

Phe Lys Gly Lys Ala Thr Leu Thr Val Asp Lys Ser Ser Thr Ala
1               5                   10                  15

Tyr Met Glu Leu Leu Ser Leu Thr Ser Glu Asp Ser Ala Val Tyr Tyr
            20                  25                  30

Phe

<210> SEQ ID NO 16
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Val Gln Leu Leu Glu Ser Gly Pro Glu Leu Val Lys Pro Gly Ala Ser
1               5                   10                  15

Met Lys Ile Ser Cys Lys Ala Ser Gly Tyr Ser Phe Thr Asp Tyr Thr
            20                  25                  30

Met Asn Trp Val Lys Gln Ser His Gly Lys Asn Leu Glu Trp Ile Gly
        35                  40                  45

Leu Ile Asn Pro Tyr Asn Gly Phe Thr Ile Tyr Asn Gln Lys Phe Lys
    50                  55                  60

Gly Lys Ala Thr Leu Thr Val Asp Lys Ser Ser Ser Thr Ala Tyr Met
65                  70                  75                  80

Glu Leu Leu Ser Leu Thr Ser Glu Asp Ser Ala Val Tyr Tyr Phe Ile
                85                  90                  95

Arg Ala His Tyr Asp Gly Arg Val Phe Trp Gly Gln Gly Thr Thr Leu
            100                 105                 110

Thr Val Ser Ser
        115

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acgttcggag gggggaccaa gctagaaata aaacgg                          36

<210> SEQ ID NO 18
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18
cagagccttg tacacagtaa tggaaacacc tatttacat                       39

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic -continued oligonucleotide

<400> SEQUENCE: 19
ctgatctacc aagtttccaa c                                               21

<210> SEQ ID NO 20
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tgctctcaaa ttacacattt tcctccc                                         27

<210> SEQ ID NO 21
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgtgaactag tgatgaccca gtctccactc tccctgcctg tcagtcttgg agatcaagcc     60
tccgtctctt gcagatctag t                                               81

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
cggtacctgc agaagccagg ccagtctcca aagctc                               36

<210> SEQ ID NO 23
<211> LENGTH: 102
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
cgattttctg gggtcccaga caggttcagt ggcagtggat cagggacaga tttcacactc     60
aagatcacca gagtggaggc tgaggatctg ggagtttatt tc                       102

<210> SEQ ID NO 24
<211> LENGTH: 342
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
tgtgaactag tgatgaccca gtctccactc tccctgcctg tcagtcttgg agatcaagcc     60
tccgtctctt gcagatctag tcagagcctt gtacacagta atggaaacac ctatttacat    120
cggtacctgc agaagccagg ccagtctcca aagctcctga tctaccaagt ttccaaccga    180

```
tttctgggg tcccagacag gttcagtggc agtggatcag ggacagattt cacactcaag    240
atcaccagag tggaggctga ggatctggga gtttatttct gctctcaaat tacacatttt    300
cctcccacgt tcggagggg gaccaagcta gaaataaaac gg                       342
```

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Thr Phe Gly Gly Gly Thr Lys Leu Glu Ile Lys Arg
1               5                   10
```

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Gln Ser Leu Val His Ser Asn Gly Asn Thr Tyr Leu His
1               5                   10
```

<210> SEQ ID NO 27
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Leu Ile Tyr Gln Val Ser Asn
1               5
```

<210> SEQ ID NO 28
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

```
Cys Ser Gln Ile Thr His Phe Pro Pro
1               5
```

<210> SEQ ID NO 29
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

```
Cys Glu Leu Val Met Thr Gln Ser Pro Leu Ser Leu Pro Val Ser Leu
1               5                   10                  15

Gly Asp Gln Ala Ser Val Ser Cys Arg Ser Ser
            20                  25
```

```
<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Arg Tyr Leu Gln Lys Pro Gly Gln Ser Pro Lys Leu
1               5                   10

<210> SEQ ID NO 31
<211> LENGTH: 34
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Arg Phe Ser Gly Val Pro Asp Arg Phe Ser Gly Ser Gly Ser Gly Thr
1               5                   10                  15

Asp Phe Thr Leu Lys Ile Thr Arg Val Glu Ala Glu Asp Leu Gly Val
            20                  25                  30

Tyr Phe

<210> SEQ ID NO 32
<211> LENGTH: 114
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Cys Glu Leu Val Met Thr Gln Ser Pro Leu Ser Leu Pro Val Ser Leu
1               5                   10                  15

Gly Asp Gln Ala Ser Val Ser Cys Arg Ser Ser Gln Ser Leu Val His
            20                  25                  30

Ser Asn Gly Asn Thr Tyr Leu His Arg Tyr Leu Gln Lys Pro Gly Gln
        35                  40                  45

Ser Pro Lys Leu Leu Ile Tyr Gln Val Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Thr Arg Val Glu Ala Glu Asp Leu Gly Val Tyr Phe Cys Ser Gln
                85                  90                  95

Ile Thr His Phe Pro Pro Thr Phe Gly Gly Gly Thr Lys Leu Glu Ile
            100                 105                 110

Lys Arg

<210> SEQ ID NO 33
<211> LENGTH: 348
<212> TYPE: DNA
<213> ORGANISM: Unknown
<220> FEATURE:
<223> OTHER INFORMATION: Description of Unknown: 10H9 monoclonal
      antibody heavy chain variable region polynucleotide
<220> FEATURE:
<221> NAME/KEY: CDS
<222> LOCATION: (1)..(348)
```

<400> SEQUENCE: 33

```
gtg cag ctg ctg gaa tct gga cct gag ctg gtg aag cct gga gct tca      48
Val Gln Leu Leu Glu Ser Gly Pro Glu Leu Val Lys Pro Gly Ala Ser
1               5                   10                  15 atg aag ata tcc tgc aag gct tct ggt tac tca ttc act gac tac acc      96
Met Lys Ile Ser Cys Lys Ala Ser Gly Tyr Ser Phe Thr Asp Tyr Thr
                20                  25                  30 atg aac tgg gtg aag cag agc cat gga aag aac ctt gag tgg att gga     144
Met Asn Trp Val Lys Gln Ser His Gly Lys Asn Leu Glu Trp Ile Gly
            35                  40                  45 ctt att aat cct tac aat ggt ttt act atc tat aat cag aag ttc aag     192
Leu Ile Asn Pro Tyr Asn Gly Phe Thr Ile Tyr Asn Gln Lys Phe Lys
        50                  55                  60 ggc aag gcc aca tta act gta gac aag tca tcc agc aca gcc tac atg     240
Gly Lys Ala Thr Leu Thr Val Asp Lys Ser Ser Ser Thr Ala Tyr Met
65                  70                  75                  80 gaa ctc ctc agt ctg aca tct gaa gac tct gca gtc tat tac ttt ata     288
Glu Leu Leu Ser Leu Thr Ser Glu Asp Ser Ala Val Tyr Tyr Phe Ile
                85                  90                  95 aga gcg cat tac gac ggg aga gtt ttt tgg ggc caa ggc acc act ctc     336
Arg Ala His Tyr Asp Gly Arg Val Phe Trp Gly Gln Gly Thr Thr Leu
                100                 105                 110 aca gtc tcc tcg                                                     348
Thr Val Ser Ser
        115
```

<210> SEQ ID NO 34
<211> LENGTH: 116
<212> TYPE: PRT
<213> ORGANISM: Unknown
<220> FEATURE:
<223> OTHER INFORMATION: Description of Unknown: 10H9 monoclonal antibody heavy chain variable region polypeptide

<400> SEQUENCE: 34

```
Val Gln Leu Leu Glu Ser Gly Pro Glu Leu Val Lys Pro Gly Ala Ser
1               5                   10                  15

Met Lys Ile Ser Cys Lys Ala Ser Gly Tyr Ser Phe Thr Asp Tyr Thr
                20                  25                  30

Met Asn Trp Val Lys Gln Ser His Gly Lys Asn Leu Glu Trp Ile Gly
            35                  40                  45

Leu Ile Asn Pro Tyr Asn Gly Phe Thr Ile Tyr Asn Gln Lys Phe Lys
        50                  55                  60

Gly Lys Ala Thr Leu Thr Val Asp Lys Ser Ser Ser Thr Ala Tyr Met
65                  70                  75                  80

Glu Leu Leu Ser Leu Thr Ser Glu Asp Ser Ala Val Tyr Tyr Phe Ile
                85                  90                  95

Arg Ala His Tyr Asp Gly Arg Val Phe Trp Gly Gln Gly Thr Thr Leu
                100                 105                 110

Thr Val Ser Ser
        115
```

<210> SEQ ID NO 35
<211> LENGTH: 342
<212> TYPE: DNA
<213> ORGANISM: Unknown
<220> FEATURE:
<223> OTHER INFORMATION: Description of Unknown: 10H9 monoclonal antibody light chain variable region polynucleotide
<220> FEATURE:
<221> NAME/KEY: CDS

<222> LOCATION: (1)..(342)

<400> SEQUENCE: 35

```
tgt gaa cta gtg atg acc cag tct cca ctc tcc ctg cct gtc agt ctt      48
Cys Glu Leu Val Met Thr Gln Ser Pro Leu Ser Leu Pro Val Ser Leu
1               5                   10                  15 gga gat caa gcc tcc gtc tct tgc aga tct agt cag agc ctt gta cac      96
Gly Asp Gln Ala Ser Val Ser Cys Arg Ser Ser Gln Ser Leu Val His
            20                  25                  30 agt aat gga aac acc tat tta cat cgg tac ctg cag aag cca ggc cag     144
Ser Asn Gly Asn Thr Tyr Leu His Arg Tyr Leu Gln Lys Pro Gly Gln
        35                  40                  45 tct cca aag ctc ctg atc tac caa gtt tcc aac cga ttt tct ggg gtc     192
Ser Pro Lys Leu Leu Ile Tyr Gln Val Ser Asn Arg Phe Ser Gly Val
    50                  55                  60 cca gac agg ttc agt ggc agt gga tca ggg aca gat ttc aca ctc aag     240
Pro Asp Arg Phe Ser Gly Ser Gly Ser Gly Thr Asp Phe Thr Leu Lys
65                  70                  75                  80 atc acc aga gtg gag gct gag gat ctg gga gtt tat ttc tgc tct caa     288
Ile Thr Arg Val Glu Ala Glu Asp Leu Gly Val Tyr Phe Cys Ser Gln
                85                  90                  95 att aca cat ttt cct ccc acg ttc gga ggg ggg acc aag cta gaa ata     336
Ile Thr His Phe Pro Pro Thr Phe Gly Gly Gly Thr Lys Leu Glu Ile
            100                 105                 110 aaa cgg                                                              342
Lys Arg
```

<210> SEQ ID NO 36
<211> LENGTH: 114
<212> TYPE: PRT
<213> ORGANISM: Unknown
<220> FEATURE:
<223> OTHER INFORMATION: Description of Unknown: 10H9 monoclonal antibody light chain variable region polypeptide

<400> SEQUENCE: 36

```
Cys Glu Leu Val Met Thr Gln Ser Pro Leu Ser Leu Pro Val Ser Leu
1               5                   10                  15

Gly Asp Gln Ala Ser Val Ser Cys Arg Ser Ser Gln Ser Leu Val His
            20                  25                  30

Ser Asn Gly Asn Thr Tyr Leu His Arg Tyr Leu Gln Lys Pro Gly Gln
        35                  40                  45

Ser Pro Lys Leu Leu Ile Tyr Gln Val Ser Asn Arg Phe Ser Gly Val
    50                  55                  60

Pro Asp Arg Phe Ser Gly Ser Gly Ser Gly Thr Asp Phe Thr Leu Lys
65                  70                  75                  80

Ile Thr Arg Val Glu Ala Glu Asp Leu Gly Val Tyr Phe Cys Ser Gln
                85                  90                  95

Ile Thr His Phe Pro Pro Thr Phe Gly Gly Gly Thr Lys Leu Glu Ile
            100                 105                 110

Lys Arg
```

ANTIBODIES TO 25-HYDROXYVITAMIN D2 AND D3

CROSS REFERENCE TO RELATED APPLICATIONS

This application is a divisional of U.S. application Ser. No. 15/915,001 filed on Mar. 7, 2018 which is a continuation of U.S. application Ser. No. 14/335,686, filed on Jul. 18, 2014, which is a continuation of U.S. application Ser. No. 13/458,847, filed on Apr. 27, 2012, which claims priority to U.S. Provisional Application No. 61/488,630, filed on May 20, 2011. All of the applications mentioned in this paragraph are incorporated herein by reference in their entirety.

TECHNICAL FIELD

Provided herein are methods and reagents for the detection or quantification of 25-hydroxyvitamin D2 and D3, methods for stabilizing vitamin D analogs, and methods for separating 25-hydroxyvitamin D2 and D3 from vitamin D binding protein in a biological sample.

BACKGROUND

Vitamin D is a steroid hormone involved in intestinal absorption of calcium and regulation of calcium homeostasis. Vitamin D is essential for the formation and maintenance of strong, healthy bones.

Vitamin D deficiency can result from inadequate exposure to the sun, inadequate alimentary intake, decreased absorption, abnormal metabolism, or vitamin D resistance. Vitamin D deficiency has been linked to rickets, osteomalacia, osteoporosis, high blood pressure, cardiovascular disease, schizophrenia, depression, nervous system diseases, diabetes, infectious diseases, asthma, allergies, cancer, and several autoimmune diseases.

Whether consumed or produced, both forms of vitamin D (D2 and D3) are metabolized by the liver to 25-hydroxyvitamin D (25(OH)D) and then converted in the liver or kidney to 1,25-dihydroxyvitamin D. Vitamin D metabolites are bound to a carrier protein in the plasma and distributed throughout the body. It is generally accepted that 25(OH)D is the metabolite that is the most reliable clinical indicator of vitamin D status because the serum 25(OH)D levels reflect the body's storage levels of vitamin D and correlate with clinical symptoms of vitamin D deficiency.

Despite the value of detection of vitamin D to health management, accurate and sensitive assays for the detection of vitamin D or its derivatives are limited. One obstacle to development of successful assays for vitamin D has been the technical difficulty in the isolation of tightly bound 25-hydroxyvitamin D3 and 25-hydroxyvitamin D2 from their vitamin D binding protein (DBP) in test biological samples. DBP is a serum glycoprotein that binds vitamin D sterols, G-actin, fatty acids and chemotactic agents. Swamy et al., Archives of Biochemistry and Biophysics 402: 14-23 (2002). In plasma, 25-hydroxyvitamin D3 and 25-hydroxyvitamin D2 have a half-life of two to three weeks, and yet are only present in less than 0.05% free form. The majority is bound to DBP with an association affinity as high as $10^9$ $M^{-1}$ which involves hydrogen binding as well as hydrophobic interactions.

Another obstacle in developing a competitive binding immunoassay for vitamin D is the instability of the vitamin D analog used to compete for antibody binding sites with the vitamin D in biological samples. Vitamin D in the absence of DBP is highly unstable in biological samples or buffered solutions.

There thus exists a need for assay methods that accurately detect and/or quantify vitamin D and vitamin D derivatives present in biological samples in either free form or bound to DBP.

SUMMARY

Provided herein are antigenic molecules that can be used to generate antibodies capable of binding to vitamin D-derived molecules. In some embodiments, the antigenic molecule may be conjugated to a carrier protein to form an antigenic compound. Carrier protein conjugation to the antigenic molecule may occur through the use of a chemical linker. In some embodiments the antigenic protein may give rise to antibodies, such as monoclonal antibodies, that bind to different vitamin D derivatives. Many of the described antigenic molecules incorporate a vitamin D-C22 immunogen (FIG. 1(a)). More specifically, disclosed herein are vitamin D-C22 immunogens conjugated to bovine serum albumin (BSA) to produce vitamin D-C22 diaminobutane-suberoyl-BSA (vitamin D-C22 BSA) (FIG. 1(c)). Alternatively, vitamin D-C22 may be conjugated to KLH to produce vitamin D-C22 diaminobutane-suberoyl-KLH (vit D-C22 KLH) (FIG. 1(d)). The described antigenic molecules and antigenic compounds provided herein may be used to produce antigen-reactive antibodies in a mammal, such as a mouse. In turn, the immunized mammals may be used as a source of B cells to produce clonal hybridomas cell lines that produce antigen-reactive monoclonal antibodies.

Also disclosed herein are isolated antibodies and antigen-binding fragments thereof, that can bind a vitamin D derivative, such as 25-hydroxyvitamin D2 and/or 25-hydroxyvitamin D3, or a 25-hydroxyvitamin D analog, such as a vitamin D-C22 immunogenic molecule or compound, In some embodiments the described antibodies are monoclonal antibodies. In some aspects the described antibodies and antigen-binding fragments have a heavy chain CDR1 having the amino acid sequence of SEQ ID NO: 10, a heavy chain CDR2 having the amino acid sequence of SEQ ID NO: 11, a heavy chain CDR3 having the amino acid sequence of SEQ ID NO: 12, a light chain CDR1 having the amino acid sequence of SEQ ID NO: 26, a light chain CDR2 having the amino acid sequence of SEQ ID NO: 27, and a light chain CDR3 having the amino acid sequence of SEQ ID NO: 28. Such an antibody is exemplified by the monoclonal antibody 10H9 that is described herein. As will be further described, the antibodies provided herein, although monoclonal in nature, have the ability to preferentially bind more than one antigen. In this regard, some of the antibodies provided herein can bind to 25-hydroxyvitamin D2 and 25-hydroxyvitamin D3 in an essentially indistinguishable manner. Also provided are polynucleotides that encode the described antibodies and antigen-binding fragments and vectors for propagation and/or expression of the described polynucleotides.

Further provided herein are methods for detecting vitamin D deficiency in a subject by determining the level of total 25-hydroxyvitamin D in a biological sample derived from the subject wherein a decrease between the level in the biological sample relative to the level in a normal control or a threshold level of 30 ng/mL is indicative of a vitamin D deficiency in the subject.

Also provided herein are methods for treating a subject suspected of having a vitamin D deficiency by determining the level of total 25-hydroxyvitamin D in a biological sample derived from the subject and, in the event a decrease between the level in the biological sample relative to the level in a normal control or a threshold level of 30 ng/mL is detected, administering to the subject a treatment for vitamin D deficiency.

Also disclosed herein are methods for monitoring progression, regression, or stabilization of vitamin D deficiency in a subject in need thereof by determining the level of total 25-hydroxyvitamin D in a first biological sample derived from the subject at a first time and then determining the level of total 25-hydroxyvitamin D in a second biological sample derived from the subject at a second time later than the first time wherein a decrease between the level in the first biological sample and the level in the second biological sample is indicative of progression or worsening of a vitamin D deficiency in the subject, wherein little or no change between the level in the first biological sample and the level in the second biological sample is indicative of stabilization of a vitamin D deficiency in the subject, and wherein an increase between the level in the first biological sample and the level in the second biological sample is indicative of regression or improvement of a vitamin D deficiency in the subject.

Also provided herein are methods for monitoring treatment of vitamin D deficiency in a subject in need thereof by determining the level of total 25-hydroxyvitamin D in a first biological sample derived from the subject at a first time and then determining the level of total 25-hydroxyvitamin D in a second biological sample derived from the subject at a second time later than the first time and following treatment of the subject for said vitamin D deficiency wherein an increase in or stabilization of the level in the second biological sample relative to the level in the first biological sample is indicative of efficacy of the treatment of the vitamin D deficiency in said subject, and wherein a decrease in the level in the second biological sample relative to the level in the first biological sample is indicative of inefficacy of the treatment of the vitamin D deficiency in said subject.

Methods for stabilizing 25-hydroxyvitamin D analogs by contacting the 25-hydroxyvitamin D analog with 8-anilino-1-naphthalene sulfonate (ANS) are disclosed. The ANS may be in the form of ANS acid or a salt (e.g., ANS sodium salt, ANS potassium salt, ANS hemimagnesium salt or ANS ammonium salt).

Also provided herein are methods for detecting vitamin D deficiency in a subject. The methods for detecting vitamin D deficiency in a subject involve determining the level of total 25-hydroxyvitamin D in a biological sample derived from the subject by combining the biological sample and a displacement buffer. In preferred embodiments, the displacement buffer contains 8-anilino-1-naphthalene sulfonate (ANS). The ANS may be in the form of ANS acid or a salt (e.g., ANS sodium salt, ANS potassium salt, ANS hemimagnesium salt or ANS ammonium salt). The displacement buffer may further contain ethylene glycol. In some embodiments, the displacement buffer contains ANS and methanol. In some preferred embodiments, the displacement buffer contains ANS, ethylene glycol, and methanol. Next, an antibody or antigen-binding fragment that preferentially binds a vitamin D derivative, such as 25-hydroxyvitamin D2 and/or 25-hydroxyvitamin D3, or a 25-hydroxyvitamin D analog, such as a vitamin D-C22 immunogenic molecule or compound, conjugated to a first label is combined with the assay mixture. The antibody or antigen-binding fragment that preferentially binds a vitamin D derivative, such as 25-hydroxyvitamin D2 and/or 25-hydroxyvitamin D3, or a 25-hydroxyvitamin D analog, such as a vitamin D-C22 immunogenic molecule or compound, is preferably an antibody or antigen-binding fragment as described herein, for example, an antibody or antigen-binding fragment comprising a Lc CDR1 of SEQ ID NO: 26, a Lc CDR2 of SEQ ID NO: 27, and a Lc CDR3 of SEQ ID NO: 28, a Hc CDR1 of SEQ ID NO: 10, a Hc CDR2 of SEQ ID NO: 11 and a Hc CDR3 of SEQ ID NO: 12. In preferred embodiments, the antibody is monoclonal antibody 10H9. Next a 25-hydroxyvitamin D analog having a second label is combined with the assay mixture. The 25-hydroxyvitamin D analog can be present in a stabilization buffer comprising 8-anilino-1-naphthalene sulfonate (ANS). The ANS may be in the form of ANS acid or a salt (e.g., ANS sodium salt, ANS potassium salt, ANS hemimagnesium salt or ANS ammonium salt). In some embodiments, the 25-hydroxyvitamin D analog is conjugated to a carrier protein. A solid phase support conjugated to an antibody that recognizes the second label also is combined with the assay mixture. The level of total 25-hydroxyvitamin D in the biological sample is determined by measuring the signal emitted by the first label, wherein a reduced level of total 25-hydroxyvitamin D in the biological sample relative to the level in a normal control or a threshold level of 30 ng/mL is indicative of a vitamin D deficiency in the subject.

BRIEF DESCRIPTION OF THE DRAWINGS

FIG. 1 depicts the chemical structure of vitamin D-C22 molecules and antigenic compounds. FIG. 1(a) depicts an unconjugated vitamin D-C22 molecule. FIG. 1(b) provides a representation of a general vitamin D-C22 antigenic compound. FIGS. 1(c) and 1(d) show specific vitamin D-C22 antigenic compounds, where the vitamin D-C22 molecule is conjugated to either BSA or KLH by a linker: D-C22 diaminobutane-suberoyl-BSA (FIG. 1(c)) and D-C22 diaminobutane-suberoyl-KLH (FIG. 1(d)).

Figure 14:
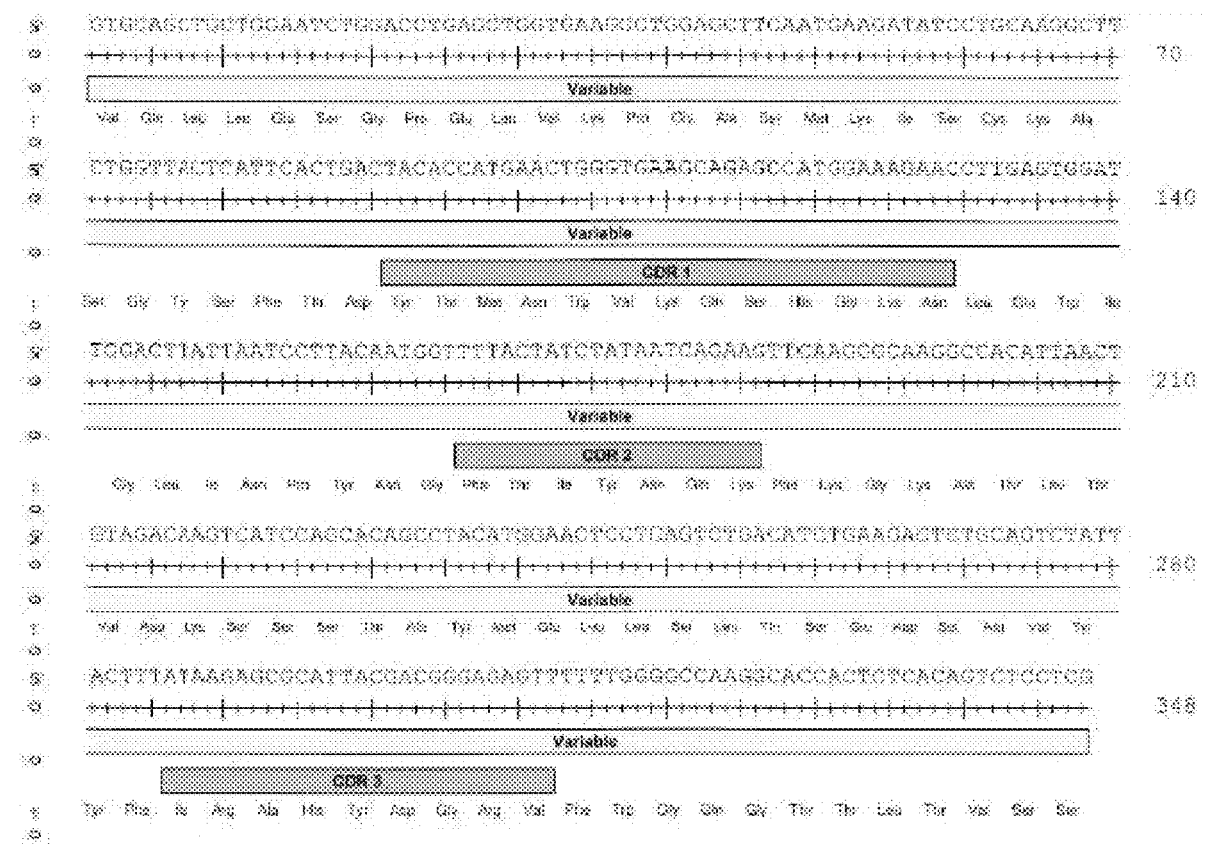

FIG. 14 provides an annotated description of the 10H9 monoclonal antibody heavy chain variable region (SEQ ID NOS 33-34, respectively, in order of appearance).

Figure 15:
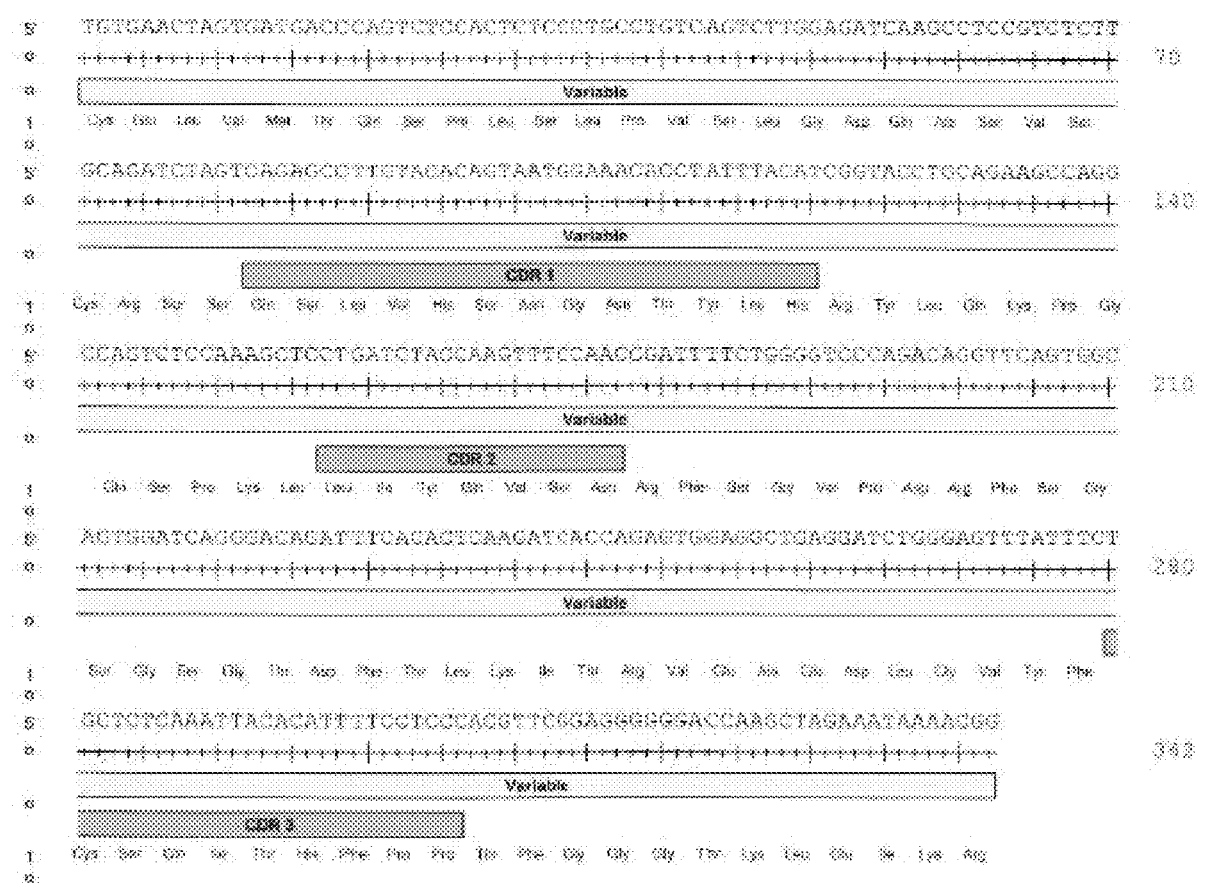

FIG. 15 provides an annotated description of the 10H9 monoclonal antibody light chain variable region (SEQ ID NOS 35-36, respectively, in order of appearance).

DETAILED DESCRIPTION OF ILLUSTRATIVE EMBODIMENTS

Figure 2:
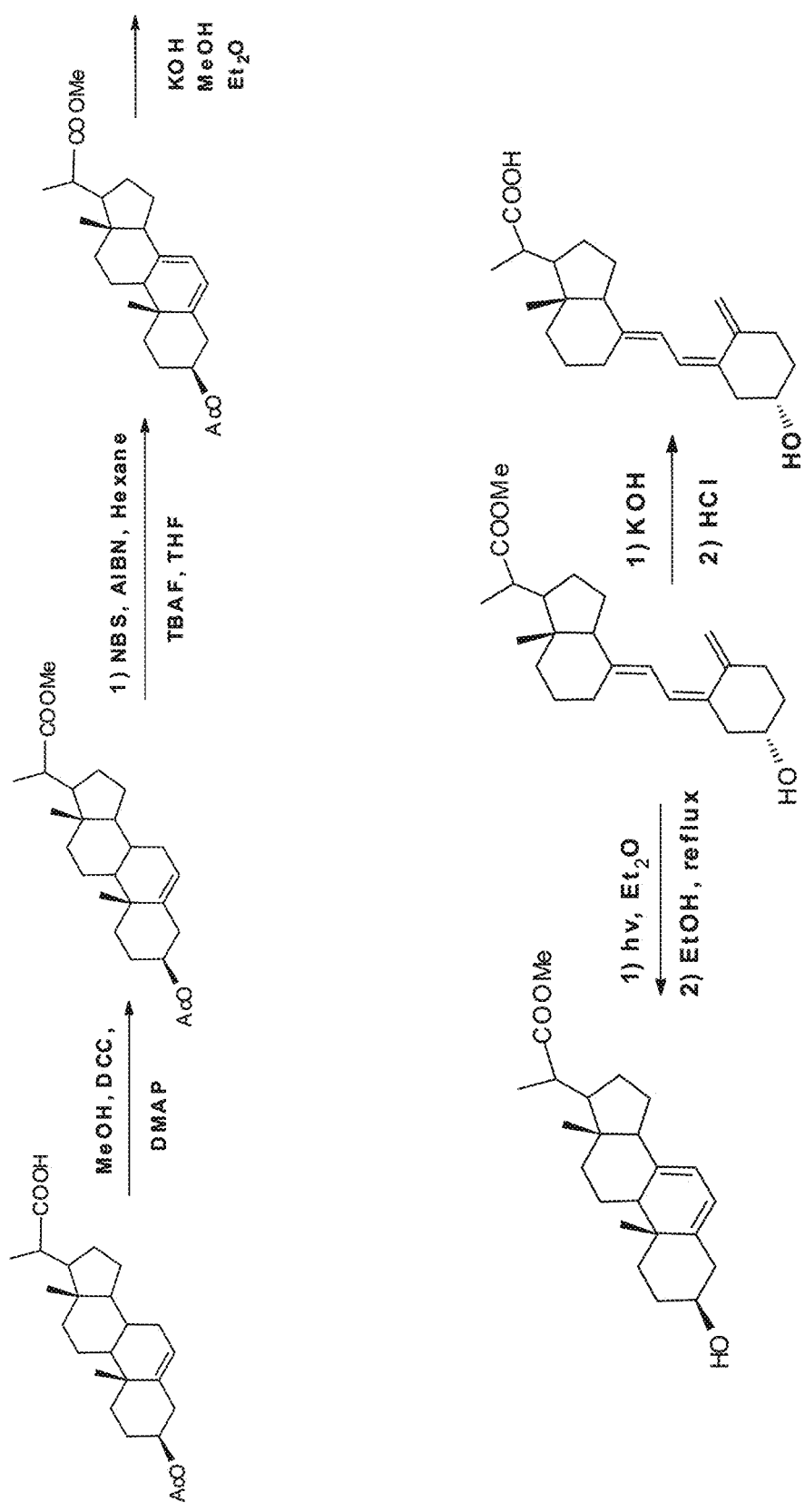
FIG. 2 shows a chemical process for producing vit D-C22 acid.

Various terms relating to aspects of the description are used throughout the specification and claims. Such terms are to be given their ordinary meaning in the art unless otherwise indicated. Other specifically defined terms are to be construed in a manner consistent with the definitions provided herein.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of up to 20% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective testing measurements.

"Isolated" means altered "by the hand of man" from the natural state. If a molecule or composition occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated" as the term is employed herein.

"Polynucleotide," synonymously referred to as "nucleic acid molecule" or "nucleic acids," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Substantially the same" with respect to nucleic acid or amino acid sequences, means at least 65% identity between two or more sequences. Preferably, the term refers to at least 70% identity between two or more sequences, more preferably at least 75% identity, more preferably at least 80% identity, more preferably at least 85% identity, more preferably at least 90% identity, more preferably at least 91% identity, more preferably at least 92% identity, more preferably at least 93% identity, more preferably at least 94% identity, more preferably at least 95% identity, more preferably at least 96% identity, more preferably at least 97% identity, more preferably at least 98% identity, and more preferably at least 99% or greater identity. Such identity may be determined using mBLAST algorithm (Altschul et al. (1990) Proc. Natl. Acad. Sci. USA 87:2264-8; Karlin and Altschul (1993) Proc. Natl. Acad. Sci. USA 90:5873-7).

A "vector" is a replicon, such as plasmid, phage, cosmid, or virus in which another nucleic acid segment may be operably inserted so as to bring about the replication or expression of the segment.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences may be operably linked to promoters or regulatory sequences in a sense or antisense orientation. The term "operably linked" is sometimes applied to the arrangement of other transcription control elements (e.g., enhancers) in an expression vector.

A cell has been "transformed" when exogenous or heterologous nucleic acids such as DNA have been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations. In some examples provided herein, cells are transformed by transfecting the cells with DNA.

"Polypeptide" refers to any peptide or protein comprising two or more amino acids joined to each other by peptide bonds or modified peptide bonds, i.e., peptide isosteres. "Polypeptide" refers to both short chains, commonly referred to as peptides, oligopeptides or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts, monographs, and research literature. Modifications may occur anywhere in a polypeptide, including the peptide backbone, the amino acid side-chains and the amino or carboxyl termini. The same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural posttranslational processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination (See, for instance, Proteins—Structure and Molecular Properties, 2nd Ed., T. E. Creighton, W. H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., Analysis for Protein Modifications and Nonprotein Cofactors, Meth Enzymol (1990) 182:626-646 and Rattan et al., Protein Synthesis: Posttranslational Modifications and Aging, Ann NY Acad Sci (1992) 663:48-62).

"Biomolecules" include proteins, polypeptides, nucleic acids, lipids, monosaccharides, polysaccharides, and all fragments, analogs, homologs, conjugates, and derivatives thereof.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression or production of an antibody or antigen-binding fragment thereof may be within the cytoplasm of the cell, or into the extracellular milieu such as the growth medium of a cell culture.

"Antibody" refers to all isotypes of immunoglobulins (IgG, IgA, IgE, IgM, IgD, and IgY) including various monomeric and polymeric forms of each isotype, unless otherwise specified.

An antigen-binding fragment is any proteinaceous structure that may exhibit binding affinity for a particular antigen. Some antigen-binding fragments are composed of portions of intact antibodies that retain antigen-binding specificity of the parent antibody molecule. For example, antigen-binding fragments may comprise at least one variable region (either a heavy chain or light chain variable region) or one or more CDRs of an antibody known to bind a particular antigen. Examples of suitable antigen-binding fragments include, without limitation diabodies and single-chain molecules as well as Fab, F(ab')2, Fc, Fabc, and Fv molecules, single chain (Sc) antibodies, individual antibody light chains, individual antibody heavy chains, chimeric fusions between antibody chains or CDRs and other proteins, protein scaffolds, or molecules, heavy chain monomers or dimers, light chain monomers or dimers, dimers consisting of one heavy and one light chain, and the like. All antibody isotypes may be used to produce antigen-binding fragments. Additionally, antigen-binding fragments may include non-antibody proteinaceous frameworks that may successfully incorporate polypeptide segments in an orientation that confers affinity for a given antigen of interest, such as protein scaffolds. Antigen-binding fragments may be recombinantly produced or produced by enzymatic or chemical cleavage of intact antibodies. The phrase "an antibody or antigen-binding fragment thereof" may be used to denote that a given antigen-binding fragment incorporates one or more amino acid segments of the antibody referred to in the phrase.

"Antibody compositions" refer to antibodies or binding fragments thereof that are coupled with at least one pharmaceutically acceptable carrier, chemotherapeutic agent, or diagnostic moiety, as described herein.

"Specific binding" refers to the ability of an antibody, or antigen-binding fragment, to bind to a particular biomolecule with an affinity that is greater than that with which it may bind other biomolecules. This term is used synonymously with "preferential" binding, meaning that a particular binding interaction is favored by the interacting components over a majority of, but not all, other such interactions.

The embodiments described herein are not limited to particular methods, reagents, compounds, compositions or biological systems, which can, of course, vary. Furthermore, the terminology used herein is for the purpose of describing particular antibodies or antigen-binding fragments only, and is not intended to be limiting.

Antigenic Molecules and Antigenic Compounds

Provided herein are antigenic molecules that can be used to generate antibodies capable of binding to vitamin D-derived molecules. In some embodiments, the antigenic molecule may be conjugated to a carrier protein to form an antigenic compound. Carrier protein conjugation to the antigenic molecule may occur through the use of a chemical linker. In some embodiments the antigenic protein may give rise to antibodies that bind equally to different vitamin D derivatives.

The antigenic molecules described herein are based on the use of a vitamin D 22 carbon derivative (vitamin D-C22), which includes a C22 carboxy group when unconjugated, as depicted in FIG. 1(a) (Hollis et al., Clin. Chem. 39(3):529-33 (1993)). Antigenic molecules based on this compound retain the common portion of 25-hydroxyvitamin D2 and 25-hydroxyvitamin D3, as these molecules differ structurally by only their side arms, which are absent from the vitamin D-C22 molecule. Given the structural commonalities between vitamin D-C22, 25-hydroxyvitamin D2 and 25-hydroxyvitamin D3, antibodies generated using antigens based on vitamin D-C22 may be able to recognize both 25-hydroxyvitamin D2 and 25-hydroxyvitamin D3.

The antigenic molecules disclosed herein may be combined with carrier proteins to produce antigenic compounds.

The use of carrier proteins may be useful to enhance the ability of the antigenic molecule to elicit an immune response in a mammal. For example carrier proteins may allow for a longer half-life in the host or allow for multiple antigenic molecules to be attached to the same carrier, thus producing a multivalent antigenic compound. In some embodiments, the described antigenic molecules may be affixed directly to the protein carrier. For example, vitamin D-C22 may be directly conjugated to bovine serum albumin (BSA). In some embodiments, a plurality of antigenic molecules may be conjugated to the same carrier protein to produce a multivalent antigenic compound. The number of antigenic molecules that may be conjugated to a given protein carrier will vary based on the carrier used. For example, BSA will accommodate the linkage of a relatively modest number of antigenic molecules, perhaps about 10 to about 25; alternatively, a carrier such as keyhole limpet hemocyanin (KLH) may accommodate about 200 to about 300 antigenic molecules. In one embodiment, vitamin D-C22 is conjugated to BSA such that from about 7 to about 21 antigenic molecules are conjugated to the carrier. In one embodiment, vitamin D-C22 is conjugated to BSA such that from about 12 to about 16 antigenic molecules are conjugated to the carrier. In another such embodiment, about 14 vitamin D-C22 molecules are conjugated to a BSA carrier. Those skilled in the art will understand that a wide variety of carrier proteins may be used for the purposes described herein. Some suitable carriers include, KLH, PEGylated KLH, *Concholepas concholepas* hemocyanin (CCH), cationized BSA, and ovalbumin to name only a few. In some embodiments the antigenic molecules are conjugated to the carrier protein via amine groups present on the carrier protein. Conjugation chemistry of this nature is commonly known to those skilled in the art.

Another aspect of the antigenic compounds described herein may be a chemical linker that allows for indirect conjugation of a described antigenic molecule to a described carrier protein. The chemical linker may be comprised of alkyl, aryl, alkyloxy, amide, sulfonamide or carbonyl or peptide groups. The conjugation of the vitamin D derivative to the protein may be achieved by reaction between amino groups of the protein and a reactive N-hydroxysuccinimide ester (NHS ester) group of the vitamin d derivative. The length of the linker may vary depending on the carrier used and the number of antigenic molecules conjugated to the carrier. In other embodiments, however, the same antigen molecule may be used with the same linker for conjugation to a variety of carrier proteins, such as BSA or KLH. In some embodiments, the linker is composed of a linear chain having the formula

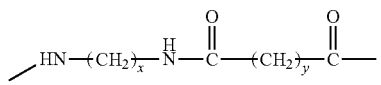

where x and y can vary, independently, from about 1 to about 12. This provides for a general antigenic compound having the formula depicted in FIG. 1(*b*). In some embodiments x may be 3 and y may be 6. In some embodiments x may be 3 and y may be 7. In some embodiments x may be 4 and y may be 7. In some embodiments x may be 5 and y may be 7. In some embodiments x may be 4 and y may be 6. In some embodiments x may be 5 and y may be 6. In some embodiments x may be 3 and y may be 5. In some embodiments x may be 4 and y may be 5. In some embodiments x may be 5 and y may be 5. In some embodiments x may be 3 and y may be 4. In some embodiments x may be 4 and y may be 4. In some embodiments x may be 5 and y may be 4. In some embodiments, the linker is used to conjugate vitamin D-C22 and BSA to produce vitamin D-C22 diaminobutane-suberoyl-BSA (vit D-C22 BSA) (FIG. 1(*c*)). In another embodiment the linker is used to conjugate vitamin D-C22 and KLH to produce vitamin D-C22 diaminobutane-suberoyl-KLH (vit D-C22 KLH) (FIG. 1(*d*)).

The antigenic molecules and antigenic compounds provided herein may be used to produce antigen-reactive antibodies in a mammal. Mammals that may be used to produce antibodies include mouse, rat, goat, horse, swine, bovine, rabbit, donkey, human, and the like. In one embodiment, the mammal is a mouse. Mammals having antigen positive sera may be used as a source of antibody producing B-cells that may be isolated and used to produce long-lived antibody producing cells, such as hybridomas cells. In some embodiments, B cells isolated from immunized mice may be used to produce hybridomas cells that produce antibodies that bind to vitamin D-C22 or vitamin D derivatives.

Antibodies

Described herein are isolated antibodies or antigen-binding fragments that preferentially bind a vitamin D derivative, such as 25-hydroxyvitamin D2 and/or 25-hydroxyvitamin D3, or a 25-hydroxyvitamin D analog, such as a vitamin D-C22 immunogenic molecule or compound. In one embodiment, the antibody or antigen-binding fragment thereof is a monoclonal antibody or antigen-binding fragment.

There are five classes of immunoglobulins wherein the primary structure of the heavy chain, in the Fc region, determines the immunoglobulin class. Specifically, the alpha, delta, epsilon, gamma, and mu chains correspond to IgA, IgD, IgE, IgG and IgM isotypes, respectively. The described antibodies or antigen-binding fragments include all isotypes and synthetic multimers of the four-chain immunoglobulin structure. The described antibodies or antigen-binding fragments also include the IgY isotype generally found in hen or turkey serum and hen or turkey egg yolk. Antibodies or antigen-binding fragments non-covalently, preferentially, and reversibly bind an antigen.

The antibodies or antigen-binding fragments of the disclosed subject matter may be derived from any species. For example, the antibodies or antigen-binding fragments may be derived from mouse, rat, goat, horse, swine, bovine, rabbit, donkey, human, and the like. In some embodiments the antibodies and antigen-binding fragments are derived from a mouse. In some embodiments the antibodies and antigen-binding fragments are derived from a mouse immunized with an immunogenic compound described herein. In some embodiments the antibodies and antigen-binding fragments are derived from a mouse immunized with vitamin D-C22 BSA. In some embodiments the antibodies are monoclonal antibodies produced using the immunogenic molecules or compounds described herein. The described monoclonal antibodies may be derived from a mouse immunized with any one or more of the immunogenic molecules or compounds described herein. For example, a monoclonal antibody, or an antigen-binding fragment thereof, capable of preferentially binding to a vitamin D derivative, such as 25-hydroxyvitamin D2 and/or 25-hydroxyvitamin D3, or a 25-hydroxyvitamin D analog, such as a vitamin D-C22 immunogenic molecule or compound may be derived from a mouse immunized with a vitamin D-C22 immunogenic molecule or compound.

In some embodiments, the antibodies or antigen-binding fragments may be chimeric. As used herein, the term "chimeric" antibody, or antigen-binding fragment, means an antibody, or antigen-binding fragment thereof, having at least some portion of at least one variable domain derived from the antibody amino acid sequence of a non-human mammal, a rodent, or a reptile, while the remaining portions of the antibody, or antigen-binding fragment thereof, are derived from a human. For example, a chimeric antibody may comprise a mouse antigen binding domain with a human Fc or other such structural domain.

In some embodiments the described antibodies may be humanized. For example, the CDRs of a human antibody may be replaced with the heavy and light chain CDRs described herein to produce an antibody, or antigen-binding fragment thereof, that same the same or substantially similar binding characteristics to the antibodies described herein, but is composed of human constant and framework regions. Methods for producing such antibodies are commonly known to those skilled in the art and, thus should be considered to be within the scope of this disclosure.

The antibodies or antigen-binding fragments described herein may be labeled or otherwise conjugated to various chemical or biomolecule moieties, for example, for diagnostic applications. The moieties may be detectable labels, for example, chemiluminescent labels (e.g., acridinium esters and sulfonamides, luminol and isoluminol), phosphorescent labels, fluorescent labels (e.g., FITC), electrochemiluminescent label (e.g, ruthenium (II) chelates), cloned enzyme donor, photosensitizer particle or chemiluminescer particle for luminescent oxygen channeling immunoassay (LOCI), lanthanide chelate for time-resolved fluorescence immunoassay (TR-FIA), radiolabels, biotin, digoxigenin, enzymes and the like, for example, radionuclides, such as, but not limited to, tritium, carbon-14, lead-212, bismuth-212, astatine-211, iodine-131, scandium-47, rhenium-186, rhenium-188, yttrium-90, iodine-123, iodine-124, iodine-125, bromine-77, indium-111, and fissionable nuclides such as boron-10 or an actinide. In some embodiments enzymes may be conjugated to the described antibodies or antigen-binding proteins for the purposes of detecting bound antibody in a sample. Such enzyme conjugates include, but are not limited to, alkaline phosphatase (AP), horseradish peroxidase, beta-galactosidase and glucose-6-phosphate dehydrogenase (G6PDH). Other enzymes used to determine antibody binding in solution-based immunoassays would be understood by those skilled in the art to be suitable for use as a conjugate for the antibodies and antigen-binding fragments described herein. In addition, compounds such as acridinium esters may also be conjugated to the provided antibodies and antigen-binding fragments to allow for detection in an immunoassay.

Antibody binding is primarily determined by the six CDR regions, especially H chain CDR3 (Kala et al., 132 J. Biochem. 535-41 (2002); Morea et al., 275 J. Mol. Biol. 269-94 (1998); and, Chothia et al., 196 J. Mol. Biol. 901-17 (1987)). Antibody framework regions, however, can play a role in antigen-antibody interactions (Panka et al., 85 Proc. Natl. Acad. Sci. USA 3080-4 (1988)), particularly in influencing the conformation of CDR loops (Foote et al., 224 J. Mol. Biol. 487-99 (1992)). Thus, the described antibodies or antigen-binding fragments may comprise any combination of H or L chain CDR or FWR regions that confer preferential binding for 25-hydroxyvitamin D2 and/or 25-hydroxyvitamin D3 or vitamin D-C22-based immunogens. Domain shuffling experiments, which are routinely carried out in the art (Jirholt et al., 215 Gene 471-6 (1998); Soderlind et al., 18 Nature Biotechnology 852-6 (2000)), may be employed to generate antibodies that preferentially bind 25-hydroxyvitamin D2 and/or 25-hydroxyvitamin D3 or vitamin D-C22-based immunogens according to the specifications described and exemplified herein. Antibodies or antigen-binding fragments generated by such domain shuffling experiments are within the scope of the antibodies or antigen-binding fragments described herein. Furthermore, CDRs may also be arranged to bind a given antigen by engineering antibody-like proteins to serve as CDR scaffolding (Nicaise et al., 13 Protein Sci. 1882 (2004)). Such antigen-binding proteins are within the scope of the antibodies described herein.

The antibodies or antigen-binding fragments described herein can occur in a variety of forms, but will include one or more of the antibody segments shown in Table 1.

Table 1. Antibody segments of the described antibodies and antigen-binding fragments thereof ("Lc" denotes light chain and "Hc" denotes heavy chain).

| 10H9 Antibody Segment | Amino Acid SEQ ID NO. | DNA SEQ ID NO. |
|---|---|---|
| Lc CDR1 | 26 | 18 |
| Lc CDR2 | 27 | 19 |
| Lc CDR3 | 28 | 20 |
| Lc FWR1 | 29 | 21 |
| Lc FWR2 | 30 | 22 |
| Lc FWR3 | 31 | 23 |
| Lc FWR4 | 25 | 17 |
| Lc variable domain | 32 | 24 |
| Hc CDR1 | 10 | 2 |
| Hc CDR2 | 11 | 3 |
| Hc CDR3 | 12 | 4 |
| Hc FWR1 | 13 | 5 |
| Hc FWR2 | 14 | 6 |
| Hc FWR3 | 15 | 7 |
| Hc FWR4 | 9 | 1 |
| Hc variable domain | 16 | 8 |

In some embodiments, the antibodies or antigen-binding fragments may include a heavy chain CDR1 amino acid sequence substantially the same as, or identical to, SEQ ID NO: 10. In some embodiments, the antibodies or antigen-binding fragments may include a heavy chain CDR2 amino acid sequence substantially the same as, or identical to, SEQ ID NO: 11. In some embodiments, antibodies or antigen-binding fragments may include a heavy chain CDR3 amino acid sequence substantially the same as, or identical to, SEQ ID NO: 12. In some embodiments, antibodies or antigen-binding fragments may include a light chain CDR1 amino acid sequence substantially the same as, or identical to, SEQ ID NO: 26. In some embodiments, antibodies or antigen-binding fragments may include a light chain CDR2 amino acid sequence substantially the same as, or identical to, SEQ ID NO: 27. In some embodiments, antibodies or antigen-binding fragments may include a light chain CDR3 amino acid sequence substantially the same as, or identical to, SEQ ID NO: 28. In some embodiments, antibodies or antigen-binding fragments may include a heavy chain CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12. In some embodiments, antibodies or antigen-binding fragments may include a light chain CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28. In some embodiments, antibodies or antigen-binding fragments may include a heavy chain and a light chain, wherein the heavy chain has a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12; and the light chain has a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28. Antigen-binding arrangements of CDRs may also be engineered using antibody-like proteins as CDR scaffolding. Such engineered antigen-binding proteins are within the scope of the disclosure.

In some embodiments, antibodies or antigen-binding fragments may include a heavy chain FWR1 amino acid sequence substantially the same as, or identical to, SEQ ID NO: 13. In some embodiments, antibodies or antigen-binding fragments may include a heavy chain FWR2 amino acid sequence substantially the same as, or identical to, SEQ ID NO: 14. In some embodiments, antibodies or antigen-binding fragments may include a heavy chain FWR3 amino acid sequence substantially the same as, or identical to, SEQ ID NO: 15. In some embodiments, antibodies or antigen-binding fragments may include a light chain FWR1 amino acid sequence substantially the same as, or identical to, SEQ ID NO: 29. In some embodiments, antibodies or antigen-binding fragments may include a light chain FWR2 amino acid sequence substantially the same as, or identical to, SEQ ID NO: 30. In some embodiments, antibodies or antigen-binding fragments may include a light chain FWR3 amino acid sequence substantially the same as, or identical to, SEQ ID NO: 31. In some embodiments, antibodies or antigen-binding fragments may include a heavy chain having a FWR1 amino acid sequence that is substantially the same as, or identical to, SEQ ID NO: 13; a FWR2 amino acid sequence that is substantially the same as, or identical to, SEQ ID NO: 14; and a FWR3 amino acid sequence that is substantially the same as, or identical to, SEQ ID NO: 15. In some embodiments, antibodies or antigen-binding fragments may include a light chain having a FWR1 amino acid sequence that is substantially the same as, or identical to, SEQ ID NO: 29; a FWR2 amino acid sequence that is substantially the same as, or identical to, SEQ ID NO: 30; and a FWR3 amino acid sequence that is substantially the same as, or identical to, SEQ ID NO: 31. In some embodiments, antibodies or antigen-binding fragments may include a heavy chain and a light chain, wherein the heavy chain includes a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15; and the light chain includes a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31.

In some embodiments, antibodies or antigen-binding fragments may include a heavy chain having a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12; a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15. In some embodiments, the antibodies or antigen-binding fragments include a light chain having a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28; a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31. In some embodiments, the antibodies or antigen-binding fragments include a heavy and a light chain, wherein the heavy chain includes a CDR1 amino acid sequence substantially the same as, or identical to, SEQ ID NO: 10; a CDR2 amino acid sequence substantially the same as, or identical to, SEQ ID NO: 11; and a CDR3 amino acid sequence substantially the same as, or identical to, SEQ ID NO: 12; a FWR1 amino acid sequence substantially the same as, or identical to, SEQ ID NO: 13; a FWR2 amino acid sequence substantially the same as, or identical to, SEQ ID NO: 14; and a FWR3 amino acid sequence substantially the same as, or identical to, SEQ ID NO: 15; and the light chain includes a CDR1 amino acid sequence substantially the same as, or identical to, SEQ ID NO: 26; a CDR2 amino acid sequence substantially the same as, or identical to, SEQ ID NO: 27; and a CDR3 amino acid sequence substantially the same as, or identical to, SEQ ID NO: 28; a FWR1 amino acid sequence substantially the same as, or identical to, SEQ ID NO: 29; a FWR2 amino acid sequence substantially the same as, or identical to, SEQ ID NO: 30; and a FWR3 amino acid sequence substantially the same as, or identical to, SEQ ID NO: 31. Antigen-binding arrangements of CDRs and FWRs may also be engineered using antibody-like proteins as CDR scaffolding. Such engineered antigen-binding proteins are within the scope of the disclosure.

In some embodiments, the antibodies or antigen-binding fragments described herein have a murine heavy chain. In some embodiments, the antibodies or antigen-binding fragments described herein have a murine light chain. The described antibodies or antigen-binding fragments may have a heavy and a light chain, wherein the heavy chain is a murine heavy chain and the light chain is a murine light chain. In some embodiments, the antibodies or antigen-binding fragments described herein have a murine IgG1 heavy chain. In some embodiments, the antibodies or antigen-binding fragments described herein have a murine Ig kappa light chain. The described antibodies or antigen-binding fragments may have a heavy and a light chain, wherein the heavy chain is a murine IgG1 heavy chain and the light chain is a murine Ig kappa chain.

Polynucleotides Encoding the Antibodies

Also described are polynucleotides that encode antibodies or antigen-binding fragments that preferentially bind a vitamin D derivative, such as 25-hydroxyvitamin D2 and/or 25-hydroxyvitamin D3, or a 25-hydroxyvitamin D analog, such as a vitamin D-C22 immunogenic molecule or compound. The described polynucleotides can occur in a variety of forms and, therefore, may be native polynucleotides, recombinant polynucleotides (such as cDNA), or synthetically produced polynucleotides. In some embodiments, the polynucleotides encode an antibody or antigen-binding fragment thereof having a heavy chain CDR1 sequence substantially the same as, or identical to, SEQ ID NO: 10, for example SEQ ID NO: 2. In some embodiments, the polynucleotides encode an antibody or antigen-binding fragment thereof having a heavy chain CDR2 substantially the same as, or identical to, SEQ ID NO: 11, for example SEQ ID NO: 3. In some embodiments, the polynucleotides encode an antibody or antigen-binding fragment thereof having a heavy chain CDR3 substantially the same as, or identical to, SEQ ID NO: 12, for example SEQ ID NO: 4. In some embodiments, the polynucleotides encode an antibody or antigen-binding fragment thereof having a light chain CDR1 substantially the same as, or identical to, SEQ ID NO: 26, for example SEQ ID NO: 18. In some embodiments, the polynucleotides encode an antibody or antigen-binding fragment thereof having a light chain CDR2 substantially the same as, or identical to, SEQ ID NO: 27, for example SEQ ID NO: 19. In some embodiments, the polynucleotides encode an antibody or antigen-binding fragment thereof having a light chain CDR3 substantially the same as, or identical to, SEQ ID NO: 28, for example SEQ ID NO: 20. The polynucleotides may encode an antibody or antigen-binding fragment thereof having a heavy chain with a CDR1 substantially the same as, or identical to, SEQ ID NO: 10, for example SEQ ID NO: 2; a CDR2 substantially the same as, or identical to, SEQ ID NO: 11, for example SEQ ID NO: 3; and a CDR3 substantially the same as, or identical to, SEQ ID NO: 12, for example SEQ ID NO: 4. The polynucleotides may encode an antibody or antigen-binding fragment thereof having a light chain CDR1 substantially the same as, or identical to, SEQ ID NO: 26, for example SEQ ID NO: 18; a CDR2 substantially the same as, or identical to, SEQ ID NO: 27, for example SEQ ID NO: 19; and a CDR3 substantially the same as, or identical to, SEQ ID NO: 28, for example SEQ ID NO: 20. The polynucleotides may encode an antibody or antigen-binding fragment thereof having a heavy chain CDR1 substantially the same as, or identical to, SEQ ID NO: 10, for example SEQ ID NO: 2; a CDR2 encoded by a nucleotide sequence substantially the same as, or identical to, SEQ ID NO: 11, for example SEQ ID NO: 3; and a CDR3 encoded by a nucleotide sequence substantially the same as, or identical to, SEQ ID NO: 12, for example SEQ ID NO: 4; and a light chain CDR1 substantially the same as, or identical to, SEQ ID NO: 26, for example SEQ ID NO: 18; a CDR2 substantially the same as, or identical to, SEQ ID NO: 27, for example SEQ ID NO: 19; and a CDR3 substantially the same as, or identical to, SEQ ID NO: 28, for example SEQ ID NO: 20.

In some embodiments, the polynucleotides encode an antibody or antigen-binding fragment thereof having a heavy chain FWR1 substantially the same as, or identical to, SEQ ID NO: 13, for example SEQ ID NO: 5. In some embodiments, the polynucleotides encode an antibody or antigen-binding fragment thereof having a heavy chain FWR2 substantially the same as, or identical to, SEQ ID NO: 14, for example SEQ ID NO: 6. In some embodiments, the polynucleotides encode an antibody or antigen-binding fragment thereof having a heavy chain FWR3 substantially the same as, or identical to, SEQ ID NO: 15, for example SEQ ID NO: 7. In some embodiments, the polynucleotides encode an antibody or antigen-binding fragment thereof having a light chain FWR1 substantially the same as, or identical to, SEQ ID NO: 29, for example SEQ ID NO: 21. In some embodiments, the polynucleotides encode an antibody or antigen-binding fragment thereof having a light chain FWR2 substantially the same as, or identical to, SEQ ID NO: 30, for example SEQ ID NO: 22. In some embodiments, the polynucleotides encode an antibody or antigen-binding fragment thereof having a light chain FWR3 substantially the same as, or identical to, SEQ ID NO: 31, for example SEQ ID NO: 23. In some embodiments, the polynucleotides encode an antibody or antigen-binding fragment thereof having a heavy chain FWR1 substantially the same as, or identical to, SEQ ID NO: 13, for example SEQ ID NO: 5; a FWR2 substantially the same as, or identical to, SEQ ID NO: 14, for example SEQ ID NO: 6; and a FWR3 substantially the same as, or identical to, SEQ ID NO: 15, for example SEQ ID NO: 7. In some embodiments, the polynucleotides encode an antibody or antigen-binding fragment thereof having a light FWR1 substantially the same as, or identical to, SEQ ID NO: 29, for example SEQ ID NO: 21; a FWR2 substantially the same as, or identical to, SEQ ID NO: 30, for example SEQ ID NO: 22; and a FWR3 substantially the same as, or identical to, SEQ ID NO: 31, for example SEQ ID NO: 23. In some embodiments, the polynucleotides encode an antibody or antigen-binding fragment thereof having a heavy chain and a light chain, wherein a heavy chain FWR1 is substantially the same as, or identical to, SEQ ID NO: 13, for example SEQ ID NO: 5; a heavy chain FWR2 is substantially the same as, or identical to, SEQ ID NO: 14, for example SEQ ID NO: 6; and a heavy chain FWR3 is substantially the same as, or identical to, SEQ ID NO: 15, for example SEQ ID NO: 7; and a light chain FWR1 is substantially the same as, or identical to, SEQ ID NO: 29, for example SEQ ID NO: 21; a light chain FWR2 is substantially the same as, or identical to, SEQ ID NO: 30, for example SEQ ID NO: 22; and a light chain FWR3 substantially the same as, or identical to, SEQ ID NO: 31, for example SEQ ID NO: 23.

In some embodiments, the polynucleotides encode an antibody or antigen-binding fragment thereof having a heavy chain CDR1 substantially the same as, or identical to, SEQ ID NO: 10, for example SEQ ID NO: 2; a heavy chain CDR2 substantially the same as, or identical to, SEQ ID NO: 11, for example SEQ ID NO: 3; and a heavy chain CDR3 substantially the same as, or identical to, SEQ ID NO: 12, for example SEQ ID NO: 4; a heavy chain FWR1 substantially the same as, or identical to, SEQ ID NO: 13, for example SEQ ID NO: 5; a heavy chain FWR2 substantially the same as, or identical to, SEQ ID NO: 14, for example SEQ ID NO: 6; and a heavy chain FWR3 substantially the same as, or identical to, SEQ ID NO: 15, for example SEQ ID NO: 7. In some embodiments, the polynucleotides encode an antibody or antigen-binding fragment thereof having a light chain CDR1 substantially the same as, or identical to, SEQ ID NO: 26, for example SEQ ID NO: 18; a light chain CDR2 substantially the same as, or identical to, SEQ ID NO: 27, for example SEQ ID NO: 19; and a light chain CDR3 substantially the same as, or identical to, SEQ ID NO: 28, for example SEQ ID NO: 20; a light chain FWR1 substantially the same as, or identical to, SEQ ID NO: 29, for example SEQ ID NO: 21; a light chain FWR2 substantially the same as, or identical to, SEQ ID NO: 30, for example SEQ ID NO: 22; and a light chain FWR3 substantially the same as, or identical to, SEQ ID NO: 31, for example SEQ ID NO: 23.

In some embodiments, the polynucleotides encode an antibody or antigen-binding fragment thereof having a heavy and a light chain, wherein the polynucleotides encode a heavy chain CDR1 substantially the same as, or identical to, SEQ ID NO: 10, for example SEQ ID NO: 2; a heavy chain CDR2 substantially the same as, or identical to, SEQ ID NO: 11, for example SEQ ID NO: 3; a heavy chain CDR3 substantially the same as, or identical to, SEQ ID NO: 12, for example SEQ ID NO: 4; a heavy chain FWR1 substantially the same as, or identical to, SEQ ID NO: 13, for example SEQ ID NO: 5; a heavy chain FWR2 substantially the same as, or identical to, SEQ ID NO: 14, for example SEQ ID NO: 6; and a heavy chain FWR3 substantially the same as, or identical to, SEQ ID NO: 15, for example SEQ ID NO: 7; and a light chain CDR1 substantially the same as, or identical to, SEQ ID NO: 26, for example SEQ ID NO: 18; a light chain CDR2 substantially the same as, or identical to, SEQ ID NO: 27, for example SEQ ID NO: 19; a light chain CDR3 substantially the same as, or identical to, SEQ ID NO: 28, for example SEQ ID NO: 20; a light chain FWR1 substantially the same as, or identical to, SEQ ID NO: 29, for example SEQ ID NO: 21; a light chain FWR2 substantially the same as, or identical to, SEQ ID NO: 30, for example SEQ ID NO: 22; and a light chain FWR3 substantially the same as, or identical to, SEQ ID NO: 31, for example SEQ ID NO: 23.

Polynucleotides encoding engineered antigen-binding proteins also are within the scope of the disclosure.

In some embodiments, the polynucleotides described (and the peptides they encode) include a leader sequence. Any leader sequence known in the art may be employed. In some embodiments, the leader sequence may be, or be based on, the heavy or light chain leader sequence of an antibody. The leader sequence may include, but is not limited to, a restriction site or a translation start site.

Because of the natural sequence variation likely to exist among heavy and light chains and the genes encoding them, one would expect to find some level of variation within the amino acid sequences or the genes encoding the antibodies or antigen-binding fragments described herein, with little or no impact on their unique binding properties (e.g., specificity and affinity). Such an expectation is due in part to the degeneracy of the genetic code, as well as to the evolutionary success of conservative amino acid sequence variations, which do not appreciably alter the nature of the encoded protein. Accordingly, some embodiments include antibodies or antigen-binding fragments having 90%, 95%, 96%, 97%, 98%, or 99% homology to the antibodies or antigen-binding fragments herein. Other embodiments include antibodies that preferentially bind a vitamin D derivative, such as 25-hydroxyvitamin D2 and/or 25-hydroxyvitamin D3, or a 25-hydroxyvitamin D analog, such as a vitamin D-C22 immunogenic molecule or compound, or antigen-binding fragments of such antibodies, that have framework, scaffold, or other non-binding regions that do not share significant homology with the antibodies and antigen-binding fragments described herein, but do incorporate one or more CDRs or other sequences needed to confer binding that are 90%, 95%, 96%, 97%, 98%, or 99% homologous to such sequences described herein.

The antibodies or antigen-binding fragments described herein include variants having single or multiple amino acid substitutions, deletions, or additions that retain the biological properties (e.g., binding affinity or binding preference) of the described antibodies or antigen-binding fragments. The skilled person may produce variants having single or multiple amino acid substitutions, deletions, or additions. These variants may include: (a) variants in which one or more amino acid residues are substituted with conservative or nonconservative amino acids, (b) variants in which one or more amino acids are added to or deleted from the polypeptide, (c) variants in which one or more amino acids include a substituent group, and (d) variants in which the polypeptide is fused with another peptide or polypeptide such as a fusion partner, a protein tag or other chemical moiety, that may confer useful properties to the polypeptide, such as, for example, an epitope for an antibody, a polyhistidine sequence, a biotin moiety and the like. Antibodies or antigen-binding fragments described herein may include variants in which amino acid residues from one species are substituted for the corresponding residue in another species, either at the conserved or nonconserved positions. In other embodiments, amino acid residues at nonconserved positions are substituted with conservative or nonconservative residues. The techniques for obtaining these variants, including genetic (suppressions, deletions, mutations, etc.), chemical, and enzymatic techniques, are known to the person having ordinary skill in the art.

The antibodies or antigen-binding fragments described herein may embody several antibody isotypes, such as IgM, IgD, IgG, IgA and IgE. Antibody or antigen-binding fragment thereof specificity is largely determined by the amino acid sequence, and arrangement, of the CDRs. Therefore, the CDRs of one isotype may be transferred to another isotype without altering antigen specificity. Alternatively, techniques have been established to cause hybridomas to switch from producing one antibody isotype to another (isotype switching) without altering antigen specificity. Accordingly, such antibody isotypes are within the scope of the described antibodies or antigen-binding fragments.

The antibodies or antigen-binding fragments described herein have binding affinities (in M) for a vitamin D derivative, such as 25-hydroxyvitamin D2 and/or 25-hydroxyvitamin D3, or a 25-hydroxyvitamin D analog, such as a vitamin D-C22 immunogenic molecule or compound that include a dissociation constant ($K_D$) of less than $1\times10^{-2}$. In some embodiments, the $K_D$ is less than $1\times10^{-3}$. In other embodiments, the $K_D$ is less than $1\times10^{-4}$. In some embodiments, the $K_D$ is less than $1\times10^{-5}$. In still other embodiments, the $K_D$ is less than $1\times10^{-6}$, $2\times10^{-6}$, $3\times10^{-6}$, $4\times10^{-6}$, $5\times10^{-6}$, $6\times10^{-6}$, $7\times10^{-6}$, $8\times10^{-6}$, or $9\times10^{-6}$. In other embodiments, the $K_D$ is less than $1\times10^{-7}$, $2\times10^{-7}$, or $3\times10^{-7}$, $2\times10^{-7}$, $3\times10^{-7}$, $4\times10^{-7}$, $5\times10^{-7}$, $6\times10^{-7}$, $7\times10^{-7}$, $8\times10^{-7}$, or $9\times10^{-7}$. In other embodiments, the $K_D$ is less than $1\times10^{-8}$, $2\times10^{-8}$, $3\times10^{-8}$, $4\times10^{-8}$, $5\times10^{-8}$, $6\times10^{-8}$, $7\times10^{-8}$, $8\times10^{-8}$, or $9\times10^{-7}$. In other embodiments, the $K_D$ is less than $1\times10^{-9}$, $2\times10^{-9}$, $3\times10^{-9}$, $4\times10^{-9}$, $5\times10^{-9}$, $6\times10^{-9}$, $7\times10^{-9}$, $8\times10^{-9}$, or $9\times10^{-9}$. In other embodiments, the $K_D$ is less than $1\times10^{-10}$, $2\times10^{-10}$, $3\times10^{-10}$, $2\times10^{-10}$, $3\times10^{-10}$, $4\times10^{-10}$, $5\times10^{-10}$, $6\times10^{-10}$, $7\times10^{-10}$, $8\times10^{-10}$, or $9\times10^{-10}$. In still other embodiments, the $K_D$ is less than $1\times10^{-11}$, $2\times10^{-11}$, $3\times10^{-11}$, $4\times10^{-11}$, $5\times10^{-11}$, $6\times10^{-11}$, $7\times10^{-11}$, $8\times10^{-11}$, or $9\times10^{-11}$. In some embodiments, the $K_D$ is less than $1\times10^{-12}$. In other embodiments, the $K_D$ is less than $1\times10^{-13}$. In other embodiments, the $K_D$ is less than $1\times10^{-14}$. In still other embodiments, the $K_D$ is less than $1\times10^{-15}$.

The antibodies or antigen-binding fragments described herein, in some embodiments, have equimolar recognition of 25-hydroxyvitamin D2 and 25-hydroxyvitamin D3.

The antibodies or antigen-binding fragments described herein may be modified, e.g., by the covalent attachment of any type of molecule to the antibody or antigen-binding fragment thereof such that covalent attachment does not prevent the antibody or antigen-binding fragment thereof from binding to its epitope. Examples of suitable modifications include, but are not limited to glycosylation, acetylation, pegylation, phosphorylation, amidation, and the like. In some embodiments the antibodies or antigen-binding fragments may themselves be derivatized by known protecting/blocking groups, proteolytic cleavage, linkage to a cellular ligand or other proteins, and the like. The antibodies or antigen-binding fragments may have post-translational moieties that improve upon antibody or antigen-binding fragment thereof activity or stability. These moieties include sulfur, methyl, carbohydrate, phosphorus as well as other chemical groups commonly found on immunoglobulin molecules. Furthermore, the antibodies or antigen-binding fragments may contain one or more non-classical amino acids.

Antibodies or antigen-binding fragments described herein may be labeled with or conjugated to diagnostic labels.

Also provided are vectors comprising the polynucleotides described herein. The vectors can be expression vectors. Recombinant expression vectors containing a sequence encoding a polypeptide of interest are thus provided. The expression vector may contain one or more additional sequences such as but not limited to regulatory sequences (e.g., promoter, enhancer), a selection marker, and a polyadenylation signal. In some embodiments, the vectors may encode the heavy chain segment of an antibody or antigen-binding protein described herein. In some embodiments, the vectors may encode the light chain segment of an antibody or antigen-binding protein described herein. In some instances the heavy and light chain components may be encoded by a single vector. In other embodiments, the heavy and light chain components may be encoded by different vectors. Vectors for transforming a wide variety of host cells are well known and include, but are not limited to, plasmids, phagemids, cosmids, baculoviruses, bacmids, bacterial artificial chromosomes (BACs), yeast artificial chromosomes (YACs), as well as other bacterial, yeast and viral vectors.

Recombinant expression vectors within the scope of the description include synthetic, genomic, or cDNA-derived nucleic acid fragments that encode at least one recombinant protein which may be operably linked to suitable regulatory elements. Such regulatory elements may include a transcriptional promoter, sequences encoding suitable mRNA ribosomal binding sites, and sequences that control the termination of transcription and translation. Expression vectors, especially mammalian expression vectors, may also include one or more nontranscribed elements such as an origin of replication, a suitable promoter and enhancer linked to the gene to be expressed, other 5' or 3' flanking nontranscribed sequences, 5' or 3' nontranslated sequences (such as necessary ribosome binding sites), a polyadenylation site, splice donor and acceptor sites, or transcriptional termination sequences. An origin of replication that confers the ability to replicate in a host may also be incorporated.

The transcriptional and translational control sequences in expression vectors to be used in transforming vertebrate cells may be provided by viral sources. Exemplary vectors may be constructed as described by Okayama and Berg, 3 Mol. Cell. Biol. 280 (1983).

In some embodiments, the antibody or antigen-binding fragment-coding sequence is placed under control of a powerful constitutive promoter, such as the promoters for the following genes: hypoxanthine phosphoribosyl transferase (HPRT), adenosine deaminase, pyruvate kinase, beta-actin, human myosin, human hemoglobin, human muscle creatine, and others. In addition, many viral promoters function constitutively in eukaryotic cells and are suitable for use with the described embodiments. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. In one embodiment, the antibody or antigen-binding fragment thereof coding sequence is placed under control of an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like.

Vectors described herein may contain one or more Internal Ribosome Entry Site(s) (IRES). Inclusion of an IRES sequence into fusion vectors may be beneficial for enhancing expression of some proteins. In some embodiments the vector system will include one or more polyadenylation sites (e.g., SV40), which may be upstream or downstream of any of the aforementioned nucleic acid sequences. Vector components may be contiguously linked, or arranged in a manner that provides optimal spacing for expressing the gene products (i.e., by the introduction of "spacer" nucleotides between the ORFs), or positioned in another way. Regulatory elements, such as the IRES motif, may also be arranged to provide optimal spacing for expression.

The vectors may comprise selection markers, which are well known in the art. Selection markers include positive and negative selection markers, for example, antibiotic resistance genes (e.g., neomycin resistance gene, a hygromycin resistance gene, a kanamycin resistance gene, a tetracycline resistance gene, a penicillin resistance gene), glutamate sythase genes, HSV-TK, HSV-TK derivatives for ganciclovir selection, or bacterial purine nucleoside phosphorylase gene for 6-methylpurine selection (Gadi et al., 7 Gene Ther. 1738-1743 (2000)). A nucleic acid sequence encoding a selection marker or the cloning site may be upstream or downstream of a nucleic acid sequence encoding a polypeptide of interest or cloning site.

The vectors described herein may be used to transform various cells with the genes encoding the described antibodies or antigen-binding fragments. For example, the vectors may be used to generate antibody or antigen-binding fragment-producing cells. Thus, another aspect features host cells transformed with vectors comprising a nucleic acid sequence encoding an antibody or antigen-binding fragment thereof that binds a vitamin D derivative, such as 25-hydroxyvitamin D2 and/or 25-hydroxyvitamin D3, or a 25-hydroxyvitamin D analog, such as a vitamin D-C22 immunogenic molecule or compound such as the antibodies or antigen-binding fragments described and exemplified herein.

Numerous techniques are known in the art for the introduction of foreign genes into cells and may be used to construct the recombinant cells for purposes of carrying out the described methods, in accordance with the various embodiments described and exemplified herein. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include but are not limited to chromosome transfer (e.g., cell fusion, chromosome mediated gene transfer, micro cell mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline, 29 Pharmac. Ther. 69-92 (1985)). Calcium phosphate precipitation and polyethylene glycol (PEG)-induced fusion of bacterial protoplasts with mammalian cells may also be used to transform cells.

Cells suitable for use in the expression of the antibodies or antigen-binding fragments described herein are preferably eukaryotic cells, more preferably cells of plant, rodent, or human origin, for example but not limited to NSO, CHO, perC.6, Tk-ts13, BHK, HEK293 cells, COS-7, T98G, CV-1/EBNA, L cells, C127, 3T3, HeLa, NS1, Sp2/0 myeloma cells, and BHK cell lines, among others. In addition, expression of antibodies may be accomplished using hybridoma cells. Methods for producing hybridomas are well established in the art.

Cells transformed with expression vectors described herein may be selected or screened for recombinant expression of the antibodies or antigen-binding fragments described herein. Recombinant-positive cells are expanded and screened for subclones exhibiting a desired phenotype, such as high level expression, enhanced growth properties, or the ability to yield proteins with desired biochemical characteristics, for example, due to protein modification or altered post-translational modifications. These phenotypes may be due to inherent properties of a given subclone or to mutation. Mutations may be effected through the use of chemicals, UV-wavelength light, radiation, viruses, insertional mutagens, inhibition of DNA mismatch repair, or a combination of such methods.

Once a cell expressing the desired protein is identified, it can be expanded and selected. Transformed cells may be selected in a number of ways. For example, cells may be selected for expression of the polypeptide of interest. Cells transformed with a vector that contains a selectable marker, such as production of fluorescent protein, may be positively selected for expression of the marker. In other embodiments, the cells containing a vector with a drug resistance gene may be positively selected for the ability to grow under selective conditions.

Assays and Methods

The antibodies and antigen-binding fragments described herein may be used to detect vitamin D derivatives or analogues in a sample. In some embodiments, the antibodies and antigen-binding fragments are used to detect a vitamin D derivative, such as 25-hydroxyvitamin D2 and/or 25-hydroxyvitamin D3, or a 25-hydroxyvitamin D analog, such as a vitamin D-C22 immunogenic molecule or compound. In some embodiments, the described antibodies and antigen-binding fragments can be used to detect vitamin D derivatives or analogues in a biological sample obtained from a patient or a subject. In some embodiments the sample may be blood or a blood component, such as serum. In preferred embodiments, the patient or subject is human. In some aspects the biological sample may be obtained from a human patient or subject, for example, human blood. The described methods may be used with the antibodies and antigen-binding fragments alone, or in conjunction with other readily available antibodies or detection reagents.

Provided herein are methods for detecting vitamin D deficiency in a subject. In preferred embodiments, the subject is human. The methods comprise determining the level of total 25-hydroxyvitamin D in a biological sample derived from the subject wherein a decrease or reduction in level in the biological sample relative to the level in a normal control or to a threshold level of 30 ng/mL is indicative of a vitamin D deficiency in the subject.

25-hydroxyvitamin D can be either of two forms, 25-hydroxyvitamin D2 and 25-hydroxyvitamin D3. In preferred embodiments of the methods for detecting vitamin D deficiency in a subject, the level of 25-hydroxyvitamin D2 and 25-hydroxyvitamin D3 is determined by contacting the biological sample with an antibody or antigen-binding fragment that recognizes both 25-hydroxyvitamin D2 and 25-hydroxyvitamin D3.

Various heterogeneous and homogenous protocols, either competitive or noncompetitive, can be employed in performing the methods for detecting vitamin D deficiency in a subject. In preferred embodiments, the methods are performed by sequential competitive immunoassay. The Centaur™, Vista™, and Immulite™ are assay systems that can be used to perform a competitive immunoassay.

In accordance with the methods for detecting vitamin D deficiency in a subject, the level of total 25-hydroxyvitamin D2 and 25-hydroxyvitamin D3 in a biological sample can be detected by enhanced chemiluminescence (ECL), enzyme immunoassay (EIA), immunohistochemistry (IHC), western blot analysis, radioimmunoassay (RIA), immunofluorescence, equilibrium dialysis, immunodifferentiation, or enzyme-linked immunosorbant assay (ELISA).

In preferred embodiments of the methods for detecting vitamin D deficiency in a subject, the antibody or antigen-binding fragment used in accordance with the methods is not cross-reactive with vitamin D2 and/or vitamin D3. In preferred embodiments, the antibody or antigen-binding fragment is an antibody or antigen-binding fragment as described herein. For example, the antibody or antigen-binding fragment comprises a Lc CDR1 of SEQ ID NO: 26, a Lc CDR2 of SEQ ID NO: 27, and a Lc CDR3 of SEQ ID NO: 28, a Hc CDR1 of SEQ ID NO: 10, a Hc CDR2 of SEQ ID NO: 11 and a Hc CDR3 of SEQ ID NO: 12. In some embodiments, the antibody or antigen-binding fragment has the property of equimolar recognition for 25-hydroxyvitamin D2 and 25-hydroxyvitamin D3. In preferred embodiments, the antibody is monoclonal antibody 10H9.

Antibodies and antigen-binding fragments that recognize 25-hydroxyvitamin D2 and 25-hydroxyvitamin D3 that can be used in the methods for detecting vitamin D deficiency in a subject can be labeled, for example, with a detectable label. Exemplary labels include but are not limited to chemiluminescent compounds (e.g., an acridinium ester compound), a phosphorescent compound, a fluorescent compound, a radiolabel, biotin, or an enzyme. The mentioned exemplary labels can usually only be detected when excited by methods that include but are not limited to addition of different chemicals, stimulation by light or exposure to substrate or other compounds. When using acridinium ester compound, chemiluminescence is triggered by peroxide and acid/base resulting in a flash that can be read by appropriate instrumentation. An optional wash step may be used before initiating detectability of the detectable label.

The antibody or antigen-binding fragment can be immobilized on a solid phase support.

The antibody or antigen-binding fragment can be conjugated to a carrier protein. The complex between the antibody or antigen-binding protein and carrier protein also can be immobilized on a solid phase support.

Solid phase supports for use in the methods for detecting vitamin D deficiency in a subject include paramagnetic particles; cross-linked dextran available under the trademark SEPHADEX (Pharmacia Fine Chemicals, Piscataway, N.J.); agarose; polystyrene beads; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride. When using paramagnetic particles, some source of a magnetic field may be used to retain the particles and molecules bound directly or indirectly to the particles during an optional wash step. The molecules may be bound covalently, by salt-bridges, hydrogen bonding or another type of bond.

The biological sample can be blood, blood serum or blood plasma. In some embodiments, the biological sample may be stored under biological conditions for up to 24 hours prior to use in the methods described herein.

In some embodiments of the methods for detecting vitamin D deficiency in a subject, the biological sample is treated or combined with 8-anilino-1-naphthalene sulfonate (ANS) before contacting the biological sample with an antibody or antigen-binding fragment that recognizes both 25-hydroxyvitamin D2 and 25-hydroxyvitamin D3 Alternatively, the biological sample can be treated or combined with 8-anilino-1-naphthalene sulfonate (ANS) concurrently with contacting the biological sample with an antibody or antigen-binding fragment that recognizes both 25-hydroxyvitamin D2 and 25-hydroxyvitamin D3. The ANS may be in the form of ANS acid or a salt (e.g., ANS sodium salt, ANS potassium salt, ANS hemimagnesium salt or ANS ammonium salt). The ANS may be present, for example, in a displacement buffer. Methanol may optionally be used with the 8-anilino-1-naphthalene sulfonate (ANS) either before contacting the biological sample with an antibody or antigen-binding fragment or concurrently with contacting the biological sample with an antibody or antigen-binding fragment. Methanol may, for example, be included in the displacement buffer.

In some embodiments of the methods for detecting vitamin D deficiency in a subject, the biological sample also is treated or combined with 8-anilino-1-naphthalene sulfonate (ANS) and ethylene glycol before contacting the biological sample with an antibody that recognizes both 25-hydroxyvitamin D2 and 25-hydroxyvitamin D3 or antigen-binding fragment. Alternatively, the biological sample can be treated or combined with 8-anilino-1-naphthalene sulfonate (ANS) and ethylene glycol concurrently with contacting the biological sample with an antibody that recognizes both 25-hydroxyvitamin D2 and 25-hydroxyvitamin D3 or antigen-binding fragment. The ANS may be in the form of ANS acid or a salt (e.g., ANS sodium salt, ANS potassium salt, ANS hemimagnesium salt or ANS ammonium salt). The ANS and ethylene glycol may be present in a displacement buffer. Methanol may optionally be used with the 8-anilino-1-naphthalene sulfonate (ANS) and ethylene glycol either before contacting the biological sample with an antibody or antigen-binding fragment or concurrently with contacting the biological sample with an antibody or antigen-binding fragment. Methanol may, for example, be included in the displacement buffer.

In some embodiments of the methods for detecting vitamin D deficiency in a subject, a 25-hydroxyvitamin D analog is added to the biological sample following the contacting step. The 25-hydroxyvitamin D analog can be labeled. 25-Hydroxyvitamin D analog or labeled 25-hydroxyvitamin D analog can also be present in a stabilization buffer comprising 8-anilino-1-naphthalene sulfonate (ANS). The ANS may be in the form of ANS acid or a salt (e.g., ANS sodium salt, ANS potassium salt, ANS hemimagnesium salt or ANS ammonium salt).

The vitamin D analogs described herein may be based on the use of a vitamin D 22 carbon derivative (vitamin D-C22), which includes a C22 carboxy group when unconjugated, as depicted in FIG. 1(a) (Hollis et al., Clin. Chem. 39(3):529-33 (1993)). In some embodiments, the vitamin D analog may be vitamin D-C22. In some embodiments, the vitamin D analog may be conjugated to a carrier protein.

In some embodiments of the methods for detecting vitamin D deficiency in a subject, the described vitamin D analogs may be affixed directly to the protein carrier. For example, vitamin D-C22 may be directly conjugated to bovine serum albumin (BSA). The number of vitamin D analogs that may be conjugated to a given protein carrier will vary based on the carrier used. Those skilled in the art will understand that a wide variety of carrier proteins may be used for the purposes described herein. Some suitable carriers include, KLH, PEGylated KLH, *Concholepas concholepas* hemocyanin (CCH), cationized BSA, and ovalbumin to name only a few.

Carrier protein conjugation to the vitamin D analog may occur through the use of a chemical linker. The chemical linker may be comprised of alkyl, aryl, alkyloxy, amide, sulfonamide or carbonyl or peptide groups. The conjugation of the vitamin D analog or vitamin D derivative to the protein may be achieved by reaction between amino groups of the protein and a reactive N-hydroxysuccinimide ester (NHS ester) group of the vitamin D analog or vitamin D derivative.

In some embodiments of the methods for detecting vitamin D deficiency in a subject, vitamin D levels can be detected in 20 minutes or less starting from the point at which the biological sample is combined with the displacement buffer.

Vitamin D deficiency in the subject can be indicative of or associated with a disease. Diseases associated with vitamin D deficiency can include: rickets, osteomalacia, high blood pressure, osteoporosis, autoimmune disease, cardiovascular disease, schizophrenia, depression, nervous system disease, diabetes, infectious disease, asthma, allergy or cancer.

Also provided herein are methods for treating a subject suspected of having a vitamin D deficiency by determining the level of total 25-hydroxyvitamin D in a biological sample derived from the subject and, if a decrease between the level in the biological sample relative to the level in a normal control or a threshold level of 30 ng/mL is determined, administering to the subject a treatment for vitamin D deficiency. In preferred embodiments, the subject is human. There are several suitable ways to treat a vitamin D deficiency. Vitamin D deficiency can be treated by supplementing vitamin D intake or by phototherapy. Phototherapy can include increased exposure to natural sunlight or exposure to artificial sources of ultraviolet B light.

In preferred embodiments of the methods for treating a subject suspected of having a vitamin D deficiency, the level of 25-hydroxyvitamin D2 and 25-hydroxyvitamin D3 is determined by contacting the biological sample with an antibody or antigen-binding fragment that recognizes both 25-hydroxyvitamin D2 and 25-hydroxyvitamin D3.

Various heterogeneous and homogenous protocols, either competitive or noncompetitive, can be employed in performing the methods for treating a subject suspected of having a vitamin D deficiency. In preferred embodiments, the methods are performed by sequential competitive immunoassay. The Centaur™, Vista™, and Immulite™ are assay systems that can be used to perform a competitive immunoassay.

In accordance with the methods for treating a subject suspected of having a vitamin D deficiency, the level of total 25-hydroxyvitamin D2 and 25-hydroxyvitamin D3 in a biological sample can be detected by enhanced chemiluminescence (ECL), enzyme immunoassay (EIA), immunohistochemistry (IHC), western blot analysis, radioimmunoassay (RIA), immunofluorescence, equilibrium dialysis, immunodifferentiation, or enzyme-linked immunosorbant assay (ELISA).

In preferred embodiments of the methods for treating a subject suspected of having a vitamin D deficiency, the antibody or antigen-binding fragment used in accordance with the methods is not cross-reactive with vitamin D2 and/or vitamin D3. In preferred embodiments, the antibody or antigen-binding fragment is an antibody or antigen-binding fragment as described herein. For example, the antibody or antigen-binding fragment comprises a Lc CDR1 of SEQ ID NO: 26, a Lc CDR2 of SEQ ID NO: 27, and a Lc CDR3 of SEQ ID NO: 28, a Hc CDR1 of SEQ ID NO: 10, a Hc CDR2 of SEQ ID NO: 11 and a Hc CDR3 of SEQ ID NO: 12. In some embodiments, the antibody or antigen-binding fragment has the property of equimolar recognition for 25-hydroxyvitamin D2 and 25-hydroxyvitamin D3. In preferred embodiments, the antibody is monoclonal antibody 10H9.

Antibodies and antigen-binding fragments that recognize 25-hydroxyvitamin D2 and 25-hydroxyvitamin D3 that can be used in the methods for treating a subject suspected of having a vitamin D deficiency can be labeled, for example, with a detectable label. Exemplary labels include but are not limited to chemiluminescent compounds (e.g., an acridinium ester compound), a phosphorescent compound, a fluorescent compound, a radiolabel, biotin, or an enzyme. The mentioned exemplary labels can usually only be detected when excited by methods that include but are not limited to addition of different chemicals, stimulation by light or exposure to substrate or other compounds. When using acridinium ester compound, chemiluminescence is triggered by peroxide and acid/base resulting in a flash that can be read by appropriate instrumentation. An optional wash step may be used before initiating detectability of the detectable label.

The antibody or antigen-binding fragment can be immobilized on a solid phase support.

The antibody or antigen-binding fragment can be conjugated to a carrier protein. The complex between the antibody or antigen-binding protein and carrier protein also can be immobilized on a solid phase support.

Solid phase supports for use in the methods described herein include paramagnetic particles; cross-linked dextran available under the trademark SEPHADEX (Pharmacia Fine Chemicals, Piscataway, N.J.); agarose; polystyrene beads; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride. When using paramagnetic particles, some source of a magnetic field may be used to retain the particles and molecules bound directly or indirectly to the particles during an optional wash step. The molecules may be bound covalently, by salt-bridges, hydrogen bonding or another type of bond.

The biological sample can be blood, blood serum or blood plasma. In some embodiments, the biological sample may be stored under biological conditions for up to 24 hours prior to use in the methods described herein.

In some embodiments of the methods for treating a subject suspected of having a vitamin D deficiency, the biological sample is treated or combined with 8-anilino-1-naphthalene sulfonate (ANS) before contacting the biological sample with an antibody or antigen-binding fragment that recognizes both 25-hydroxyvitamin D2 and 25-hydroxyvitamin D3 Alternatively, the biological sample can be treated or combined with 8-anilino-1-naphthalene sulfonate (ANS) concurrently with contacting the biological sample with an antibody or antigen-binding fragment that recognizes both 25-hydroxyvitamin D2 and 25-hydroxyvitamin D3. The ANS may be in the form of ANS acid or a salt (e.g., ANS sodium salt, ANS potassium salt, ANS hemimagnesium salt or ANS ammonium salt). The ANS may be present, for example, in a displacement buffer. Methanol may optionally be used with the 8-anilino-1-naphthalene sulfonate (ANS) either before contacting the biological sample with an antibody or antigen-binding fragment or concurrently with contacting the biological sample with an antibody or antigen-binding fragment. Methanol may, for example, be included in the displacement buffer.

In some embodiments of the methods for treating a subject suspected of having a vitamin D deficiency, the biological sample also is treated or combined with 8-anilino-1-naphthalene sulfonate (ANS) and ethylene glycol before contacting the biological sample with an antibody that recognizes both 25-hydroxyvitamin D2 and 25-hydroxyvitamin D3 or antigen-binding fragment. Alternatively, the biological sample can be treated or combined with 8-anilino-1-naphthalene sulfonate (ANS) and ethylene glycol concurrently with contacting the biological sample with an antibody that recognizes both 25-hydroxyvitamin D2 and 25-hydroxyvitamin D3 or antigen-binding fragment. The ANS may be in the form of ANS acid or a salt (e.g., ANS sodium salt, ANS potassium salt, ANS hemimagnesium salt or ANS ammonium salt). The ANS and ethylene glycol may be present in a displacement buffer. Methanol may optionally be used with the 8-anilino-1-naphthalene sulfonate (ANS) and ethylene glycol either before contacting the biological sample with an antibody or antigen-binding fragment or concurrently with contacting the biological sample with an antibody or antigen-binding fragment. Methanol may, for example, be included in the displacement buffer.

In some embodiments of the methods for treating a subject suspected of having a vitamin D deficiency, a 25-hydroxyvitamin D analog is added to the biological sample following the contacting step. The 25-hydroxyvitamin D analog can be labeled. 25-Hydroxyvitamin D analog or labeled 25-hydroxyvitamin D analog can also be present in a stabilization buffer comprising 8-anilino-1-naphthalene sulfonate (ANS). The ANS may be in the form of ANS acid or a salt (e.g., ANS sodium salt, ANS potassium salt, ANS hemimagnesium salt or ANS ammonium salt).

The vitamin D analogs described herein may be based on the use of a vitamin D 22 carbon derivative (vitamin D-C22), which includes a C22 carboxy group when unconjugated, as depicted in FIG. 1($a$) (Hollis et al., Clin. Chem. 39(3):529-33 (1993)). In some embodiments, the vitamin D analog may be vitamin D-C22. In some embodiments, the vitamin D analog may be conjugated to a carrier protein.

In some embodiments of the methods for treating a subject suspected of having a vitamin D deficiency, the described vitamin D analogs may be affixed directly to the protein carrier. For example, vitamin D-C22 may be directly conjugated to bovine serum albumin (BSA). The number of vitamin D analogs that may be conjugated to a given protein carrier will vary based on the carrier used. Those skilled in the art will understand that a wide variety of carrier proteins may be used for the purposes described herein. Some suitable carriers include, KLH, PEGylated KLH, *Concholepas concholepas* hemocyanin (CCH), cationized BSA, and ovalbumin to name only a few.

Carrier protein conjugation to the vitamin D analog may occur through the use of a chemical linker. The chemical linker may be comprised of alkyl, aryl, alkyloxy, amide, sulfonamide or carbonyl or peptide groups. The conjugation of the vitamin D analog or vitamin D derivative to the protein may be achieved by reaction between amino groups of the protein and a reactive N-hydroxysuccinimide ester (NHS ester) group of the vitamin D analog or vitamin D derivative.

In some embodiments of the methods for treating a subject suspected of having a vitamin D deficiency, vitamin D levels can be detected in 20 minutes or less starting from the point at which the biological sample is combined with the displacement buffer.

Vitamin D deficiency in the subject can be indicative of or associated with a disease. Diseases associated with vitamin D deficiency can include: rickets, osteomalacia, high blood pressure, osteoporosis, autoimmune disease, cardiovascular disease, schizophrenia, depression, nervous system disease, diabetes, infectious disease, asthma, allergy or cancer.

Further provided herein are methods for monitoring progression of vitamin D deficiency in a subject in need thereof by determining the level of total 25-hydroxyvitamin D in a first biological sample derived from the subject at a first time and then determining the level of total 25-hydroxyvitamin D in a second biological sample derived from the subject at a second time later than the first time wherein a decrease between the level in the first biological sample and the level in the second biological sample is indicative of the progression of a vitamin D deficiency in the subject, wherein little or no change between the level in the first biological sample and the level in the second biological sample is indicative of stabilization of a vitamin D deficiency in the subject, and wherein an increase between the level in the first biological sample and the level in the second biological sample is indicative of regression of a vitamin D deficiency in the subject. In preferred embodiments, the subject is human.

In preferred embodiments of the methods for monitoring progression of vitamin D deficiency in a subject, the level of 25-hydroxyvitamin D2 and 25-hydroxyvitamin D3 is determined by contacting the biological sample with an antibody or antigen-binding fragment that recognizes both 25-hydroxyvitamin D2 and 25-hydroxyvitamin D3.

Various heterogeneous and homogenous protocols, either competitive or noncompetitive, can be employed in performing the methods for monitoring progression of vitamin D deficiency in a subject. In preferred embodiments, the methods are performed by competitive immunoassay. The Centaur™, Vista™, and Immulite™ are assay systems that can be used to perform a competitive immunoassay.

In accordance with the methods for monitoring progression of vitamin D deficiency in a subject, the level of total 25-hydroxyvitamin D2 and 25-hydroxyvitamin D3 in a biological sample can be detected by enhanced chemiluminescence (ECL), enzyme immunoassay (EIA), immunohistochemistry (IHC), western blot analysis, radioimmunoassay (RIA), immunofluorescence, equilibrium dialysis, immunodifferentiation, or enzyme-linked immunosorbant assay (ELISA).

In preferred embodiments of the methods for monitoring progression of vitamin D deficiency in a subject, the antibody or antigen-binding fragment used in accordance with the methods is not cross-reactive with vitamin D2 and/or vitamin D3. In preferred embodiments, the antibody or antigen-binding fragment is an antibody or antigen-binding fragment as described herein. For example, the antibody or antigen-binding fragment comprises a Lc CDR1 of SEQ ID NO: 26, a Lc CDR2 of SEQ ID NO: 27, and a Lc CDR3 of SEQ ID NO: 28, a Hc CDR1 of SEQ ID NO: 10, a Hc CDR2 of SEQ ID NO: 11 and a Hc CDR3 of SEQ ID NO: 12. In some embodiments, the antibody or antigen-binding fragment has the property of equimolar recognition for 25-hydroxyvitamin D2 and 25-hydroxyvitamin D3. In preferred embodiments, the antibody is monoclonal antibody 10H9.

Antibodies and antigen-binding fragments that recognize 25-hydroxyvitamin D2 and 25-hydroxyvitamin D3 that can be used in these methods can be labeled, for example, with a detectable label. Exemplary labels include but are not limited to chemiluminescent compounds (e.g., an acridinium ester compound), a phosphorescent compound, a fluorescent compound, a radiolabel, biotin, or an enzyme. The mentioned exemplary labels can usually only be detected when excited by methods that include but are not limited to addition of different chemicals, stimulation by light or exposure to substrate or other compounds. When using acridinium ester compound, chemiluminescence is triggered by peroxide and acid/base resulting in a flash that can be read by appropriate instrumentation. An optional wash step may be used before initiating detectability of the detectable label.

The antibody or antigen-binding fragment can be immobilized on a solid phase support.

The antibody or antigen-binding fragment can be conjugated to a carrier protein. The complex between the antibody or antigen-binding protein and carrier protein also can be immobilized on a solid phase support.

Solid phase supports for use in the methods for monitoring progression of vitamin D deficiency in a subject include paramagnetic particles; cross-linked dextran available under the trademark SEPHADEX (Pharmacia Fine Chemicals, Piscataway, N.J.); agarose; polystyrene beads; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride. When using paramagnetic particles, some source of a magnetic field may be used to retain the particles and molecules bound directly or indirectly to the particles during an optional wash step. The molecules may be bound covalently, by salt-bridges, hydrogen bonding or another type of bond.

The biological sample can be blood, blood serum or blood plasma. In some embodiments, the biological sample may be stored under biological conditions for up to 24 hours prior to use in the methods described herein.

In some embodiments of the methods for monitoring progression of vitamin D deficiency in a subject, the biological sample is treated or combined with 8-anilino-1-naphthalene sulfonate (ANS) before contacting the biological sample with an antibody or antigen-binding fragment that recognizes both 25-hydroxyvitamin D2 and 25-hydroxyvitamin D3 Alternatively, the biological sample can be treated or combined with 8-anilino-1-naphthalene sulfonate (ANS) concurrently with contacting the biological sample with an antibody or antigen-binding fragment that recognizes both 25-hydroxyvitamin D2 and 25-hydroxyvitamin D3. The ANS may be in the form of ANS acid or a salt (e.g., ANS sodium salt, ANS potassium salt, ANS hemimagnesium salt or ANS ammonium salt). The ANS may be present, for example, in a displacement buffer. Methanol may optionally be used with the 8-anilino-1-naphthalene sulfonate (ANS) either before contacting the biological sample with an antibody or antigen-binding fragment or concurrently with contacting the biological sample with an antibody or antigen-binding fragment. Methanol may, for example, be included in the displacement buffer.

In some embodiments of the methods for monitoring progression of vitamin D deficiency in a subject, the biological sample also is treated or combined with 8-anilino-1-naphthalene sulfonate (ANS) and ethylene glycol before contacting the biological sample with an antibody that recognizes both 25-hydroxyvitamin D2 and 25-hydroxyvitamin D3 or antigen-binding fragment. Alternatively, the biological sample can be treated or combined with 8-anilino-1-naphthalene sulfonate (ANS) and ethylene glycol concurrently with contacting the biological sample with an antibody that recognizes both 25-hydroxyvitamin D2 and 25-hydroxyvitamin D3 or antigen-binding fragment. The ANS may be in the form of ANS acid or a salt (e.g., ANS sodium salt, ANS potassium salt, ANS hemimagnesium salt or ANS ammonium salt). The ANS and ethylene glycol may be present in a displacement buffer. Methanol may optionally be used with the 8-anilino-1-naphthalene sulfonate (ANS) and ethylene glycol either before contacting the biological sample with an antibody or antigen-binding fragment or concurrently with contacting the biological sample with an antibody or antigen-binding fragment. Methanol may, for example, be included in the displacement buffer.

In some embodiments of the methods for monitoring progression of vitamin D deficiency in a subject, a 25-hydroxyvitamin D analog is added to the biological sample following the contacting step. The 25-hydroxyvitamin D analog can be labeled. 25-Hydroxyvitamin D analog or labeled 25-hydroxyvitamin D analog can also be present in a stabilization buffer comprising 8-anilino-1-naphthalene sulfonate (ANS). The ANS may be in the form of ANS acid or a salt (e.g., ANS sodium salt, ANS potassium salt, ANS hemimagnesium salt or ANS ammonium salt).

The vitamin D analogs described herein may be based on the use of a vitamin D 22 carbon derivative (vitamin D-C22), which includes a C22 carboxy group when unconjugated, as depicted in FIG. 1(a) (Hollis et al., Clin. Chem. 39(3):529-33 (1993)). In some embodiments, the vitamin D analog may be vitamin D-C22. In some embodiments, the vitamin D analog may be conjugated to a carrier protein.

In some embodiments of the methods for monitoring progression of vitamin D deficiency in a subject, the described vitamin D analogs may be affixed directly to the protein carrier. For example, vitamin D-C22 may be directly conjugated to bovine serum albumin (BSA). The number of vitamin D analogs that may be conjugated to a given protein carrier will vary based on the carrier used. Those skilled in the art will understand that a wide variety of carrier proteins may be used for the purposes described herein. Some suitable carriers include, KLH, PEGylated KLH, Concholepas concholepas hemocyanin (CCH), cationized BSA, and ovalbumin to name only a few.

Carrier protein conjugation to the vitamin D analog may occur through the use of a chemical linker. The conjugation of the vitamin D analog or vitamin D derivative to the protein may be achieved by reaction between amino groups of the protein and a reactive N-hydroxysuccinimide ester (NHS ester) group of the vitamin D analog or vitamin D derivative.

In some embodiments of the methods for monitoring progression of vitamin D deficiency in a subject, vitamin D levels can be detected in 20 minutes or less starting from the point at which the biological sample is combined with the displacement buffer.

Vitamin D deficiency in the subject can be indicative of or associated with a disease. Diseases associated with vitamin D deficiency can include: rickets, osteomalacia, high blood pressure, osteoporosis, autoimmune disease, cardiovascular disease, schizophrenia, depression, nervous system disease, diabetes, infectious disease, asthma, allergy or cancer.

Also provided herein are methods for monitoring treatment of vitamin D deficiency in a subject in need thereof by determining the level of total 25-hydroxyvitamin D in a first biological sample derived from the subject at a first time and then determining the level of total 25-hydroxyvitamin D in a second biological sample derived from the subject at a second time later than the first time and following treatment of the subject for said vitamin D deficiency wherein an increase in or stabilization of the level in the second biological sample relative to the level in the first biological sample is indicative of efficacy of the treatment of the vitamin D deficiency in said subject, and wherein a decrease in the level in the second biological sample relative to the level in the first biological sample is indicative of inefficacy of the treatment of the vitamin D deficiency in said subject. In preferred embodiments, the subject is human.

In preferred embodiments of the methods for monitoring treatment of vitamin D deficiency in a subject, the level of 25-hydroxyvitamin D2 and 25-hydroxyvitamin D3 is determined by contacting the biological sample with an antibody or antigen-binding fragment that recognizes both 25-hydroxyvitamin D2 and 25-hydroxyvitamin D3.

Various heterogeneous and homogenous protocols, either competitive or noncompetitive, can be employed in performing the methods for monitoring treatment of vitamin D deficiency in a subject. In preferred embodiments, the methods are performed by sequential competitive immunoassay. The Centaur™, Vista™, and Immulite™ are assay systems that can be used to perform a competitive immunoassay.

In accordance with the methods for monitoring treatment of vitamin D deficiency in a subject, the level of total 25-hydroxyvitamin D2 and 25-hydroxyvitamin D3 in a biological sample can be detected by enhanced chemiluminescence (ECL), enzyme immunoassay (EIA), immunohistochemistry (IHC), western blot analysis, radioimmunoassay (RIA), immunofluorescence, equilibrium dialysis, immunodifferentiation, or enzyme-linked immunosorbant assay (ELISA).

In preferred embodiments of the methods for monitoring treatment of vitamin D deficiency in a subject, the antibody or antigen-binding fragment used in accordance with the methods is not cross-reactive with vitamin D2 and/or vitamin D3. In preferred embodiments, the antibody or antigen-binding fragment is an antibody or antigen-binding fragment as described herein. For example, the antibody or antigen-binding fragment comprises a Lc CDR1 of SEQ ID NO: 26, a Lc CDR2 of SEQ ID NO: 27, and a Lc CDR3 of SEQ ID NO: 28, a Hc CDR1 of SEQ ID NO: 10, a Hc CDR2 of SEQ ID NO: 11 and a Hc CDR3 of SEQ ID NO: 12. In some embodiments, the antibody or antigen-binding fragment has the property of equimolar recognition for 25-hydroxyvitamin D2 and 25-hydroxyvitamin D3. In preferred embodiments, the antibody is monoclonal antibody 10H9.

Antibodies and antigen-binding fragments that recognize 25-hydroxyvitamin D2 and 25-hydroxyvitamin D3 that can be used in the methods for monitoring treatment of vitamin D deficiency in a subject can be labeled, for example, with a detectable label. Exemplary labels include but are not limited to chemiluminescent compounds (e.g., an acridinium ester compound), a phosphorescent compound, a fluorescent compound, a radiolabel, biotin, or an enzyme. The mentioned exemplary labels can usually only be detected when excited by methods that include but are not limited to addition of different chemicals, stimulation by light or exposure to substrate or other compounds. When using acridinium ester compound, chemiluminescence is triggered by peroxide and acid/base resulting in a flash that can be read by appropriate instrumentation. An optional wash step may be used before initiating detectability of the detectable label.

The antibody or antigen-binding fragment can be immobilized on a solid phase support.

The antibody or antigen-binding fragment can be conjugated to a carrier protein. The complex between the antibody or antigen-binding protein and carrier protein also can be immobilized on a solid phase support.

Solid phase supports for use in the methods described herein include paramagnetic particles; cross-linked dextran available under the trademark SEPHADEX (Pharmacia Fine Chemicals, Piscataway, N.J.); agarose; polystyrene beads; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride. When using paramagnetic particles, some source of a magnetic field may be used to retain the particles and molecules bound directly or indirectly to the particles during an optional wash step. The molecules may be bound covalently, by salt-bridges, hydrogen bonding or another type of bond.

The biological sample can be blood, blood serum or blood plasma. In some embodiments, the biological sample may be stored under biological conditions for up to 24 hours prior to use in the methods described herein.

In some embodiments of the methods for monitoring treatment of vitamin D deficiency in a subject, the biological sample is treated or combined with 8-anilino-1-naphthalene sulfonate (ANS) before contacting the biological sample with an antibody or antigen-binding fragment that recognizes both 25-hydroxyvitamin D2 and 25-hydroxyvitamin D3 Alternatively, the biological sample can be treated or combined with 8-anilino-1-naphthalene sulfonate (ANS) concurrently with contacting the biological sample with an antibody or antigen-binding fragment that recognizes both 25-hydroxyvitamin D2 and 25-hydroxyvitamin D3. The ANS may be in the form of ANS acid or a salt (e.g., ANS sodium salt, ANS potassium salt, ANS hemimagnesium salt or ANS ammonium salt). The ANS may be present, for example, in a displacement buffer. Methanol may optionally be used with the 8-anilino-1-naphthalene sulfonate (ANS) either before contacting the biological sample with an antibody or antigen-binding fragment or concurrently with contacting the biological sample with an antibody or antigen-binding fragment. Methanol may, for example, be included in the displacement buffer.

In some embodiments of the methods for monitoring treatment of vitamin D deficiency in a subject, the biological sample also is treated or combined with 8-anilino-1-naphthalene sulfonate (ANS) and ethylene glycol before contacting the biological sample with an antibody that recognizes both 25-hydroxyvitamin D2 and 25-hydroxyvitamin D3 or antigen-binding fragment. Alternatively, the biological sample can be treated or combined with 8-anilino-1-naphthalene sulfonate (ANS) and ethylene glycol concurrently with contacting the biological sample with an antibody that recognizes both 25-hydroxyvitamin D2 and 25-hydroxyvitamin D3 or antigen-binding fragment. The ANS may be in the form of ANS acid or a salt (e.g., ANS sodium salt, ANS potassium salt, ANS hemimagnesium salt or ANS ammonium salt). The ANS and ethylene glycol may be present in a displacement buffer. Methanol may optionally be used with the 8-anilino-1-naphthalene sulfonate (ANS) and ethylene glycol either before contacting the biological sample with an antibody or antigen-binding fragment or concurrently with contacting the biological sample with an antibody or antigen-binding fragment. Methanol may, for example, be included in the displacement buffer.

In some embodiments of the methods for monitoring treatment of vitamin D deficiency in a subject, a 25-hydroxyvitamin D analog is added to the biological sample following the contacting step. The 25-hydroxyvitamin D analog can be labeled. 25-hydroxyvitamin D analog or labeled 25-hydroxyvitamin D analog can also be present in a stabilization buffer comprising 8-anilino-1-naphthalene sulfonate (ANS). The ANS may be in the form of ANS acid or a salt (e.g., ANS sodium salt, ANS potassium salt, ANS hemimagnesium salt or ANS ammonium salt).

The vitamin D analogs described herein may be based on the use of a vitamin D 22 carbon derivative (vitamin D-C22), which includes a C22 carboxy group when unconjugated, as depicted in FIG. 1(a) (Hollis et al., Clin. Chem. 39(3):529-33 (1993)). In some embodiments, the vitamin D analog may be vitamin D-C22. In some embodiments, the vitamin D analog may be conjugated to a carrier protein.

In some embodiments of the methods for monitoring treatment of vitamin D deficiency in a subject, the described vitamin D analogs may be affixed directly to the protein carrier. For example, vitamin D-C22 may be directly conjugated to bovine serum albumin (BSA). The number of vitamin D analogs that may be conjugated to a given protein carrier will vary based on the carrier used. For example, BSA will accommodate the linkage of a relatively modest number of proteins, perhaps about 10 to about 25; alternatively, a carrier such as keyhole limpet hemocyanin (KLH) may accommodate about 200 to about 300 antigenic molecules. Those skilled in the art will understand that a wide variety of carrier proteins may be used for the purposes described herein. Some suitable carriers include, KLH, PEGylated KLH, *Concholepas concholepas* hemocyanin (CCH), cationized BSA, and ovalbumin to name only a few.

Carrier protein conjugation to the vitamin D analog may occur through the use of a chemical linker. The conjugation of the vitamin D analog or vitamin D derivative to the protein may be achieved by reaction between amino groups of the protein and a reactive N-hydroxysuccinimide ester (NHS ester) group of the vitamin D analog or vitamin D derivative.

In some embodiments of the methods for monitoring treatment of vitamin D deficiency in a subject, vitamin D levels can be detected in 20 minutes or less starting from the point at which the biological sample is combined with the displacement buffer.

Vitamin D deficiency in the subject can be indicative of or associated with a disease. Diseases associated with vitamin D deficiency can include: rickets, osteomalacia high blood pressure, osteoporosis, autoimmune disease, cardiovascular disease, schizophrenia, depression, nervous system disease, diabetes, infectious disease, asthma, allergy or cancer.

Also provided herein are methods for stabilizing 25-hydroxyvitamin D analog by contacting the 25-hydroxyvitamin D analog with 8-anilino-1-naphthalene sulfonate (ANS). The ANS may be in the form of ANS acid or a salt (e.g., ANS sodium salt, ANS potassium salt, ANS hemimagnesium salt or ANS ammonium salt). 25-hydroxyvitamin D analog stabilized with 8-anilino-1-naphthalene sulfonate (ANS) can be stored for greater than 2 months outside an assay system. 25-hydroxyvitamin D analog stabilized with 8-anilino-1-naphthalene sulfonate (ANS) can be stored for greater than 7 days inside an assay system.

Also provided herein are methods for detecting vitamin D deficiency in a subject. In preferred embodiments, the subject is human. Biological samples for use in the methods can be blood, blood serum or blood plasma derived from the subject. The methods for detecting vitamin D deficiency in a subject involve determining the level of total 25-hydroxyvitamin D in a biological sample derived from the subject by combining the biological sample and a displacement buffer. The biological sample may be added to the displacement buffer or vice versa to form an assay mixture. The displacement buffer displaces vitamin D from vitamin D binding protein. In preferred embodiments, the displacement buffer contains 8-anilino-1-naphthalene sulfonate (ANS). The ANS may be in the form of ANS acid or a salt (e.g., ANS sodium salt, ANS potassium salt, ANS hemimagnesium salt or ANS ammonium salt). The displacement buffer may further contain ethylene glycol. In some embodiments, the displacement buffer contains ANS and methanol. In some preferred embodiments, the displacement buffer contains ANS, ethylene glycol, and methanol.

Next, an antibody or antigen-binding fragment that preferentially binds 25-hydroxyvitamin D2, 25-hydroxyvitamin D3, or vitamin D-C22-based immunogen conjugated to a first label is combined with the assay mixture. The antibody or antigen-binding fragment may be added to the assay mixture or vice versa and becomes a component thereof. The antibody that preferentially binds 25-hydroxyvitamin D2, and 25-hydroxyvitamin D3, or vitamin D-C22-based immunogen, or antigen-binding fragment thereof, is preferably an antibody or antigen-binding fragment as described above. In preferred embodiments, the antibody or antigen-binding fragment comprises a Lc CDR1 of SEQ ID NO: 26, a Lc CDR2 of SEQ ID NO: 27, and a Lc CDR3 of SEQ ID NO: 28, a Hc CDR1 of SEQ ID NO: 10, a Hc CDR2 of SEQ ID NO: 11 and a Hc CDR3 of SEQ ID NO: 12. In preferred embodiments, the antibody is monoclonal antibody 10H9. The antibody or antigen-binding fragment that preferentially binds 25-hydroxyvitamin D2, 25-hydroxyvitamin D3, or vitamin D-C22-based immunogen can be immobilized on a solid phase support. The antibody or antigen-binding fragment that preferentially binds 25-hydroxyvitamin D2, 25-hydroxyvitamin D3, or vitamin D-C22-based immunogen can be conjugated to a carrier protein. The complex of the antibody or antigen-binding fragment that preferentially binds 25-hydroxyvitamin D2, 25-hydroxyvitamin D3, or vitamin D-C22-based immunogen and the carrier protein can also be immobilized on a solid phase support.

The first label is preferably a detectable label. The first label can be a chemiluminescent compound (e.g., an acridinium ester compound), a phosphorescent compound, a fluorescent compound, a radiolabel, biotin, or an enzyme. The mentioned exemplary labels can usually only be detected when excited by methods that include but are not limited to addition of different chemicals, stimulation by light or exposure to substrate or other compounds. When using acridinium ester compound, chemiluminescence is triggered by peroxide and acid/base resulting in a flash that can be read by appropriate instrumentation. An optional wash step may be used before initiating detectability of the detectable label.

Next a 25-hydroxyvitamin D analog having a second label is combined with the assay mixture. The 25-hydroxyvitamin D analog may be added to the assay mixture or vice versa and becomes a component thereof. The second label can be fluorescein for binding to anti-fluorescein antibody, biotin for binding to avidin, streptavidin or anti-biotin antibody, digoxigenin for binding to anti-digoxigenin antibody or other hapten and binding partner. The 25-hydroxyvitamin D analog can be present in a stabilization buffer comprising 8-anilino-1-naphthalene sulfonate (ANS). The ANS may be in the form of ANS acid or a salt (e.g., ANS sodium salt, ANS potassium salt, ANS hemimagnesium salt or ANS ammonium salt). In some embodiments, the 25-hydroxyvitamin D analog is conjugated to a carrier protein. The carrier protein can be bovine serum albumin, ovalbumin, immunoglobulin, or bovine gamma globulin IgG.

A solid phase support conjugated to an antibody that recognizes the second label also is combined with the assay mixture. The solid phase support conjugated to the antibody that recognizes the second label may be added to the assay mixture or vice versa and becomes a component of the assay mixture. The antibody that is conjugated to the solid phase support can be an antibody that binds to fluorescein.

Solid phase supports for use in the methods described herein include paramagnetic particles; cross-linked dextran available under the trademark SEPHADEX (Pharmacia Fine Chemicals, Piscataway, N.J.); agarose; polystyrene particles or beads; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride. When using paramagnetic particles, some source of a magnetic field may be used to retain the particles and molecules bound directly or indirectly to the particles during an optional wash step. The molecules may be bound covalently, by salt-bridges, hydrogen bonding or another type of bond.

The level of total 25-hydroxyvitamin D in the biological sample is determined by measuring the signal emitted by the first label, wherein a reduced level of total 25-hydroxyvitamin D in the biological sample relative to the level in a normal control or a threshold level of 30 ng/mL is indicative of a vitamin D deficiency in the subject.

The immunoreagents of any diagnostic system described herein can be provided in solution, as a liquid dispersion or as a substantially dry powder, e.g., in lyophilized form.

In some embodiments, vitamin D deficiency can be detected in 20 minutes or less starting from the point at which the biological sample is combined with the displacement buffer.

The vitamin D deficiency in the subject can be indicative of a disease. The disease can include: rickets, osteomalacia, high blood pressure, osteoporosis, autoimmune disease, cardiovascular disease, schizophrenia, depression, nervous system disease, diabetes, infectious disease, asthma, allergy or cancer.

Kits

Kits can comprise an antibody or antigen-binding fragment as described herein and instructions, for example, for collecting a biological sample from a subject and/or for using the antibody or antigen-binding fragment to determine the amount of total vitamin D in a biological sample. In preferred embodiments, the antibody or antigen-binding fragment comprises a detectable label as described herein. The kit can also comprise a vitamin D analog linked to a solid support. In some embodiments, the kit may comprise a standard curve or data set showing a correlation of the quantity or level of vitamin D with normal and/or deficient vitamin D levels.

The following examples are provided to describe the embodiments described herein with greater detail. They are intended to illustrate, not to limit, the embodiments.

EXAMPLES

Example I—Synthesis of Vitamin D-C22 Based Molecules and Compounds

To produce vitamin D-C22 based antigens a manipulable form of the molecule was necessary. To accomplish this, efforts were undertaken to produce vitamin D-C22 acid via a synthesis scheme based on that of Hollis and Napoli (Clin. Chem, 31:1815-1819 (1985)). Briefly, 23, 24-Bisnor-5-cholenic acid-3β-OL acetate (2.50 g) was reacted with methanol (0.312 mL), dicyclohexylcarbodiimide (1.59 g) and N,N-dimethylaminopyridine (160 mg) in dichloromethane (25 mL) for 3 hours to give 23, 24-bisnor-5-cholenic acid-30-OL acetate, methyl ester (1.808 g). The methyl ester (1.808 g) was brominated with N-bromosuccinimide (1.05 g)/azoisobutyronitrile (51.7 mg) in hexane (200 mL) under reflux for 30 minutes, followed by dehydrobromination with tetrabutylammonium fluoride (1 M in THF, 23.8 mL) in THE (112 mL) at room temperature for 2 hours to give 23, 24-Bisnor-5, 7-choledienic acid-3β-OL acetate methyl ester (1.21 g). 23, 24-Bisnor-5, 7-choledienic acid-30-OL acetate, methyl ester (1.21 g) was reacted with potassium hydroxide (0.50 g) in methanol (18 mL) and ethyl ether (22 mL) at room temperature for 2.5 hours to produce 23, 24-bisnor-5, 7-choledienic acid-30-OL methyl ester (0.962 g). 23, 24-Bisnor-5, 7-choledienic acid-30-OL, methyl ester (0.960 g) was irradiated under 450 w mercury lamp with a Vycor filter in ether (1100 mL) at −10 to 0° C. for 3 minutes and 30 seconds twice, then separated by column chromatography on silica gel to give pre-vitamin D-C22 methyl ester which was refluxed in ethanol (100 mL) for 3 hours to produce vitamin D-C22 methyl ester (0.389 g). Vitamin D-C22 methyl ester (249 mg) was reacted with potassium hydroxide (6.25 g) in methanol (30 mL) at 60° C. for 5 hours to give vitamin D-C22 acid (165 mg). (FIG. 2.)

Figure 3:
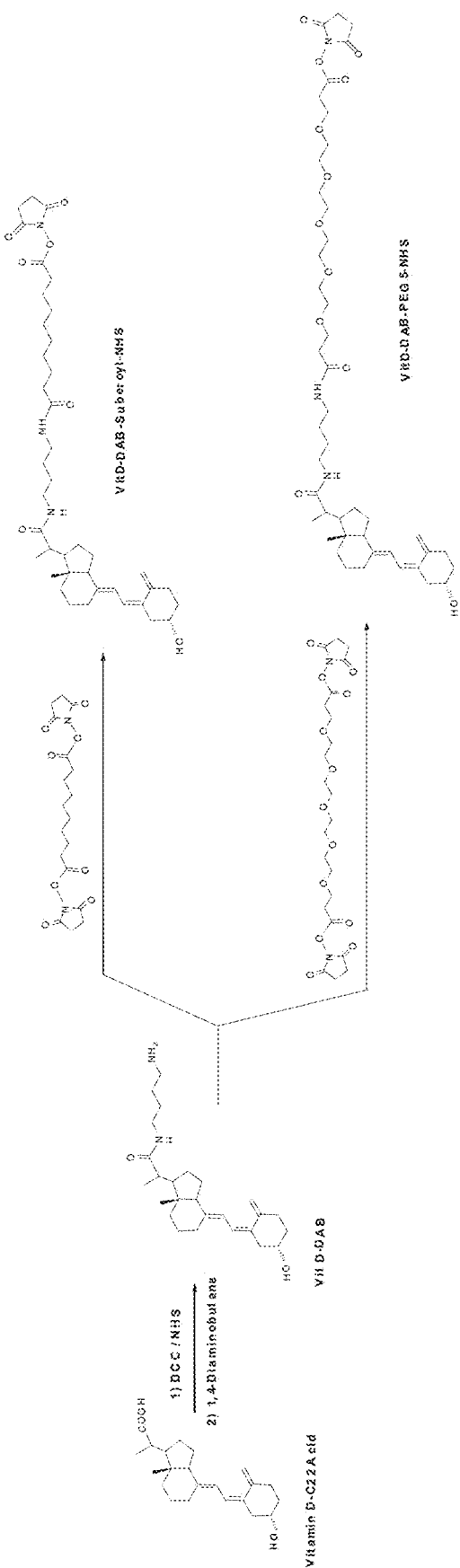
FIG. 3 depicts a chemical process for converting vit D-C22 acid to either vitD-DAB-Suberoyl-NHS or vitD-DAB-PEG5-NHS.
Figure 4:
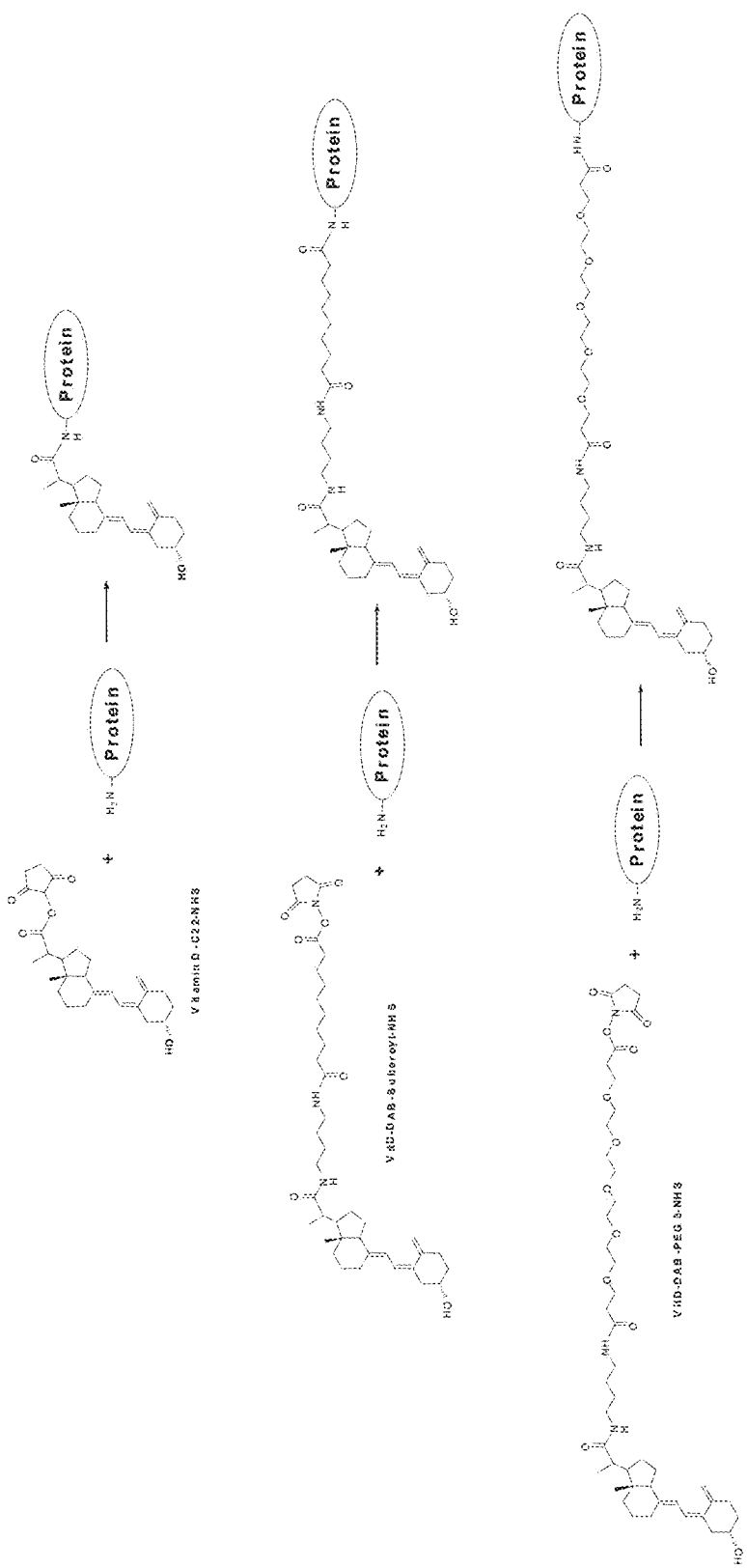
FIG. 4 illustrates chemical reaction schemes for conjugating vit D-C22, vitD-DAB-Suberoyl-NHS or vitD-DAB-PEG5-NHS to a protein carrier.

To form conjugated compounds with vitamin D-C22 an NHS precursor was needed. To achieve this vitamin D-C22 acid (165 mg) was reacted with dicyclohexycarbodiimide (116 mg) and N-hydroxysuccinimide (64 mg) in 1, 4-dioxane, then reacted with 1, 4-diaminobutane (480 uL) at room temperature for 2 hours to give vitamin D-DAB (141 mg). The protein-reactive reagents, vitamin D-DAB-Suberoyl-NHS and vitamin D-DAB-PEG5-NHS, were prepared from vitamin D-DAB by reaction with excess disuccinimidyl suberate or PEG5-Di-NHS. The NHS esters were purified by preparative reversed-phase HPLC through a C18 column. Vitamin D-DAB (30 mg) was reacted with excess of disuccinimidyl suberate (DSS, 133 mg) in DMF (1.2 mL) and triethylamine (15 uL) for 3.5 hours. The product (24.5 mg) was purified by preparative HPLC through a Synergi Hydro-RP column to produce vitamin D-DAB-Suberoyl-NHS. Vitamin D-DAB (41 mg) was reacted with excess of Bis-PEG5-NHS (282 mg) in DMF (2.0 mL) and triethylamine (20 uL) for 3.5 hours. The product (33.7 mg) was purified by preparative HPLC through a Synergi Hydro-RP column to produce vitamin D-DAB-PEG5-NHS. (FIG. 3.) Protein conjugates were prepared by reaction between the NHS ester and the lysine amino groups of the proteins as represented in FIG. 4. Vit D-DAB-Suberoyl-BSA was prepared by the reaction of Vit D-DAB-Suberoyl-NHS (5 mg) with BSA (10 mg) in a mixture of 0.1 M phosphate buffer, ph 7.5 (1 mL) and DMF (0.4 mL) at room temperature for 2 h and purified by centrifiltration using PBS, pH 7.2 for buffer exchange. MALDI-TOF mass spectrometry showed loading of 14 Vitamin D labels per BSA.

Figure 5:
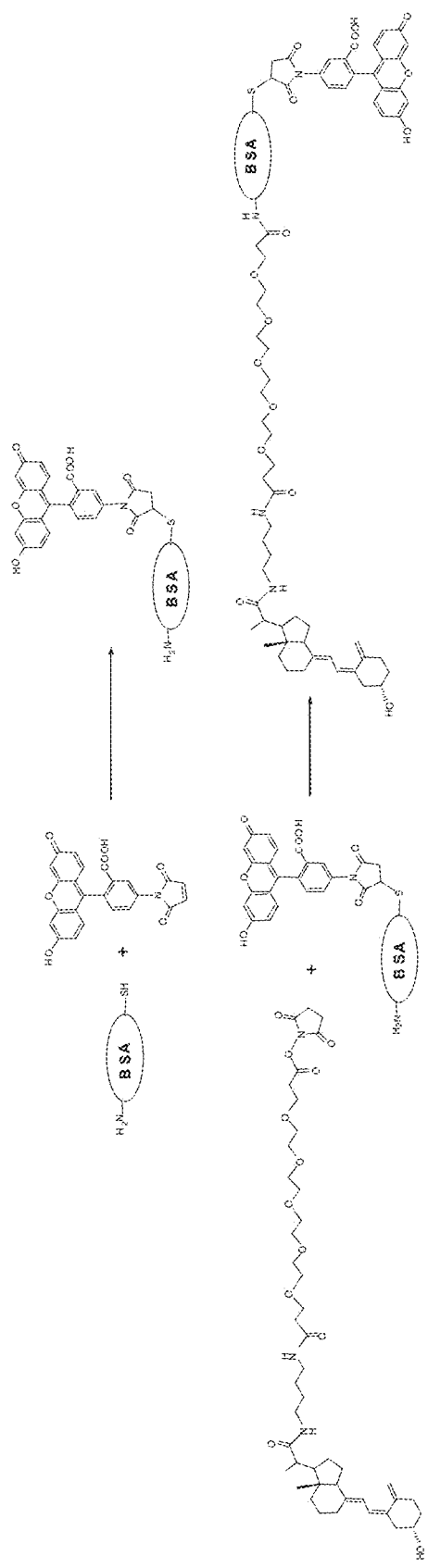
FIG. 5 shows a two-step reaction for producing a vitamin D-DAB-PEG5-BSA-Fluorescein conjugate.

Vitamin D-DAB-PEG5-BSA-Fluorescein conjugates (FIG. 5) were prepared via a two-step conjugation by reaction between the free thiol of BSA with fluorescein-5-maleimide followed by reaction of the lysine amino groups with vitamin D-DAB-PEG5-NHS. The conjugates were isolated by gel filtration using a Sephadex G25 column. It was found that the conjugate prepared using a 10:1 fluorescein-5-maleimide to BSA molar ratio followed by conjugation at 20:1 vitamin D-DAB-PEG5-NHS to BSA molar ratio produced the best Centaur® assay curves.

Vitamin D-fluorescein conjugates were prepared and used as magnetic particle coating antigen for the Centaur® assay. Good immunoassay results were obtained using a small-molecule derivative, vitamin D-DAB-PEG5-aminopentyl-thioureidyl fluorescein, MW 1208 (structure below), as a magnetic particle coating antigen.

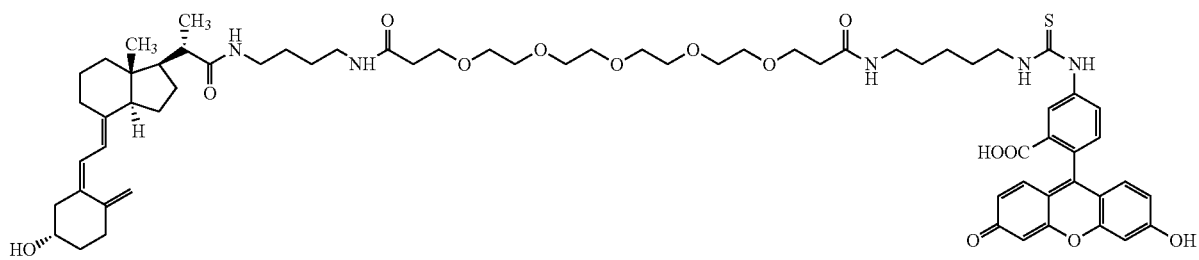 [SMILES: C=C1CC[C@H](O)C/C1=C/C=C1\CCC[C@]2(C)[C@@H]([C@H](C)C(=O)NCCCCNC(=O)CCOCCOCCOCCOCCOCCC(=O)NCCCCCNC(=S)Nc3ccc(-c4c5ccc(=O)cc-5oc5cc(O)ccc45)c(C(=O)O)c3)CC[C@@H]12]

Example II—Production of Antibodies Reactive to Vitamin D-C22 Antigenic Compounds Experiments were conducted to produce antibodies that could preferentially bind to molecules having structural aspects of the vitamin D-C22 antigenic molecule. These experiments were conducted in accordance with the method of Galfre et al. (Nature, 266:550 (1977)), as modified by Oi and Herzenberg (Selected Methods in Cellular Immunology (1980)). Initially, BALB/c mice were immunized with vitamin D-C22 BSA emulsified in Freund's Complete adjuvant followed by a secondary immunization using Freund's Incomplete adjuvant. Sera of immunized mice were collected two weeks after the secondary immunization.

Collected sera were tested for antigen reactivity by ELISA as follows: microtiter plates coated with vitamin D-C22 BSA were incubated with mouse antisera, diluted in dilution buffer, for one hour. Plates were washed and a secondary antibody (goat-anti-mouse IgG) conjugated to horseradish peroxidase (HRPO) in dilution buffer was added and incubated for 30 minutes. Plates were washed and the colorimetric substrate 3,3',5,5'-tetramethylbenzidine (TMB) was added. The generated color was stopped using 1N sulfuric acid and the optical density was measured at 450 nm. Sera from all five mice tested showed substantial reactivity relative to normal mouse serum (NMS) (Table 2).

TABLE 2

Vitamin D-C22 BSA Detection by Sera from Immunized Mice
COAT: Vit D C22 Lc-BSA (JL808) @ 500 ng/mL

|  | MOUSE # | NMS | 0 | 1 | 2 | 3 | 4 |
|---|---|---|---|---|---|---|---|
| Vit D C22 | 1:12800 | 0.055 | 2.449 | 2.406 | 1.731 | 2.325 | 3.042 |
| Initial Bleed | 1:6400 | 0.056 | 3.177 | 3.133 | 2.533 | 3.057 | 3.473 |
| May 27, 2008 | 1:3200 | 0.059 | 3.534 | 3.508 | 3.171 | 3.454 | 3.608 |
|  | 1:1600 | 0.062 | 3.578 | 3.605 | 3.532 | 3.638 | 3.687 |
|  | 1:800 | 0.069 | 3.634 | 3.731 | 3.603 | 3.708 | 3.696 |
|  | 1:400 | 0.083 | 3.602 | 3.640 | 3.633 | 3.633 | 3.441 |
|  | 1:200 | 0.110 | 3.750 | 3.693 | 3.649 | 3.663 | 3.634 |
|  | 1:100 | 0.174 | 3.747 | 3.687 | 3.625 | 3.700 | 3.652 |

Example III—Production of Monoclonal Antibodies Reactive to Vitamin D-C22 Antigenic Compounds Mice exhibiting a positive immune response to vitamin D-C22 antigens were selected for monoclonal antibody development. Briefly, spleen cells harvested from selected mice were fused with mouse Sp2/0 myeloma cells. Resulting hybridomas that produced antibodies reactive to 25-hydroxyvitamin D2 and 25-hydroxyvitamin D3 were selected and cloned at least twice by the limiting dilution procedure to obtain monoclonal antibody-producing cell lines. One monoclonal cell line that was identified and tested further was the 10H9 hybridoma.

Figure 6:
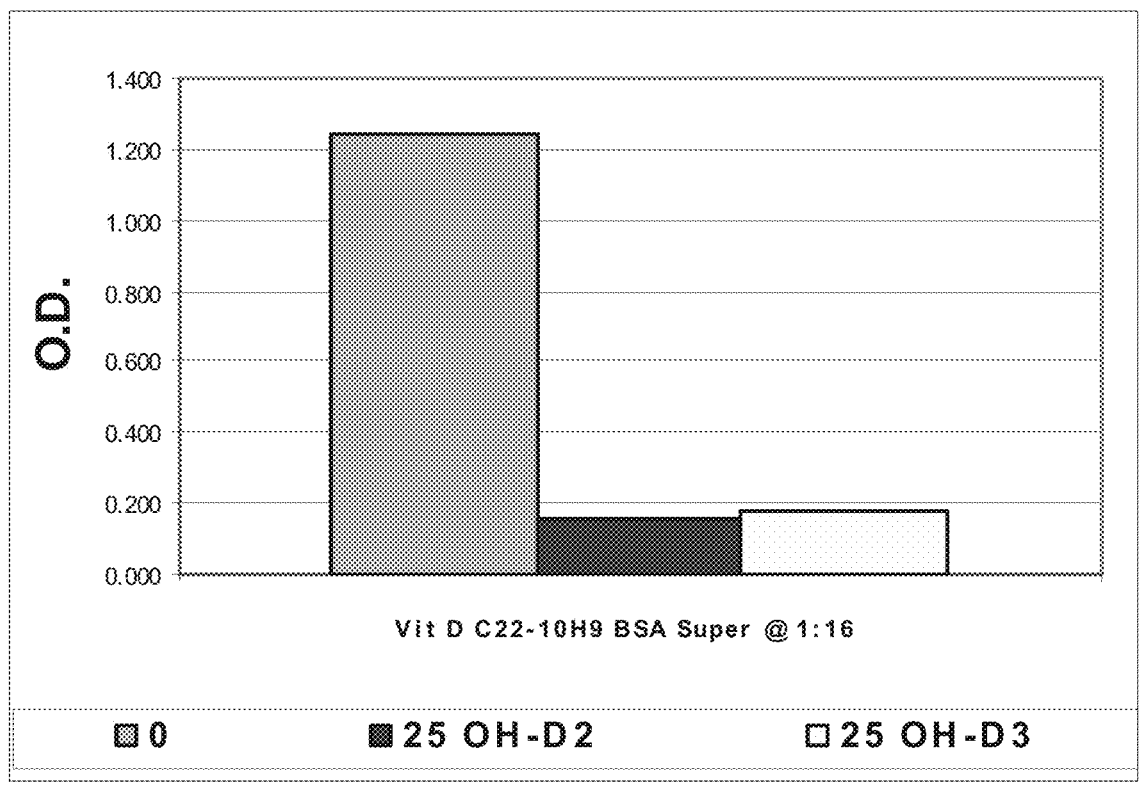
FIG. 6 provides a graphical representation of the degree of binding between vitamin D-C22-Lc KLH and the antibody from the supernatant of hybridoma 10H9 in the presence or absence of either 25-hydroxyvitamin D2 or 25-hydroxyvitamin D3.

Following isolation of hybridoma clones, studies were conducted to determine the relative ability of the antibodies to bind to both 25-hydroxyvitamin D2 and 25-hydroxyvitamin D3. To assess this, antibody displacement assays were conducted to determine the degree to which binding between vitamin D-C22 BSA and a reactive antibody raised against the antigen (10H9) could be disrupted by the presence of 25-hydroxyvitamin D2 or 25-hydroxyvitamin D3. Cell culture supernatant from the 10H9 hybridoma cell lines producing antibodies reactive to vitamin D-C22 BSA were coincubated in the presence or absence of 25-hydroxyvitamin D2 or 25-hydroxyvitamin D3 on microtiter plates coated with vitamin D-C22 KLH for 1 hour. After washing the plates, goat anti-mouse IgG-HRPO was added and incubated for 30 minutes. Plates were washed and then incubated with tetramethyl benzidine (TMB). The generated color was stopped using 1N sulfuric acid and the optical density was measured at 450 nm. As set forth in Table 3 (and as depicted in FIG. 6), antibody binding to vitamin D-C22 BSA was disrupted in a concentration-dependent manner by coincubation with either 25-hydroxyvitamin D2 or 25-hydroxyvitamin D3. Both 25-hydroxyvitamin D2 and 25-hydroxyvitamin D3 showed substantially similar binding disruption profiles which is characteristic of equimolar affinity of the antibody tested.

TABLE 3

Vitamin D-C22-Reactive Antibody Displacement
by 25-hydroxyvitamin D2 or 25-hydroxyvitamin D3.
Summary of Vit D C22-BSA super displacement assay
Coat: Vit D C22-Diaminobutane-Suberoyl-KLH
(Lot JL814) @ 50 ng/mL

| Ag @ (Final conc.) |  | 0 | 25 OH-D2 0.4 µg/mL | 25 OH-D3 0.4 µg/mL |
|---|---|---|---|---|
| Vit D C22-BSA | 1:4 | 1.997 | 0.323 | 0.384 |
| 10H9 @ | 1:16 | 1.244 | 0.154 | 0.176 |
| (Final dilution) | 1:64 | 0.672 | 0.097 | 0.105 |
|  | 1:256 | 0.313 | 0.086 | 0.090 |
| Tracer: GAM-IgG-HRP (Fc) @ 1:20K | | | | |

Figure 7:
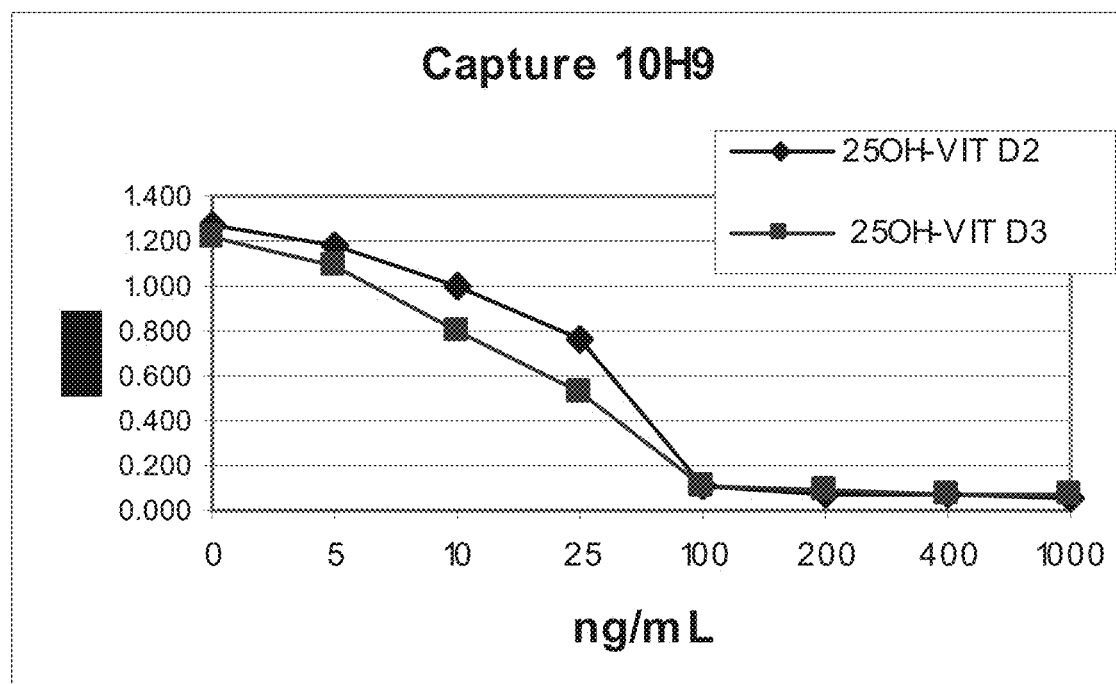
FIG. 7 is a graphical representation of the degree of binding between vitamin D C22-diaminobutane-suberoyl-alkaline phosphatase and purified 10H9 monoclonal antibody in the presence or absence of either 25-hydroxyvitamin D2 or 25-hydroxyvitamin D3.

Next, displacement experiments were conducted using purified antibody, rather than cell supernatant. In this experiment, the antibody of interest was coated directly on the microtiter plate via a two-hour incubation. Coated plates were washed and then coincubated with either 25-hydroxyvitamin D2 or 25-hydroxyvitamin D3 in the presence of alkaline phosphatase-conjugated vitamin D-C22 BSA. After 30 minutes the plates were washed and color was developed by adding the substrate p-nitrophenyl phosphate (PNPP). Optical density colored solution was measured at 405 nm. Again, 10H9 binding to vitamin D-C22 BSA was disrupted in a concentration-dependent manner by coincubation with either 25-hydroxyvitamin D2 or 25-hydroxyvitamin D3 (Table 4). Both 25-hydroxyvitamin D2 and 25-hydroxyvitamin D3 showed substantially similar binding disruption profiles which is characteristic of equimolar affinity of the antibody tested (FIG. 7).

TABLE 4

Vitamin D-C22-Reactive Antibody Displacement by
25-hydroxyvitamin D2 or 25-hydroxyvitamin D3.

| Coat 50 ul MAb @ 1 ug/mL | | 10H9 |
|---|---|---|
| 25 uL of 25OH-VIT D2 | 0 | 1.277 |
| (Fluka 1402454-13808245- | 5 | 1.189 |
| 090319MR) @ indicated final | 10 | 1.007 |
| concentrations in ng/ml | 25 | 0.771 |
|  | 100 | 0.106 |
|  | 200 | 0.080 |
|  | 400 | 0.069 |
|  | 1000 | 0.063 |
| 25 uL of 25OH-VIT D3 | 0 | 1.213 |
| (Fluka 1412212-24708001- | 5 | 1.083 |
| 090323GK) @ indicated final | 10 | 0.800 |
| concentrations in ng/ml | 25 | 0.519 |
|  | 100 | 0.115 |
|  | 200 | 0.089 |
|  | 400 | 0.077 |
|  | 1000 | 0.069 |

Example IV

Vitamin D Assay

Biological sample is added to a reaction cuvette followed by displacement buffer and allowed to react for 4.5 minutes. Monoclonal antibody conjugated to acridinium ester is added and allowed to react for 5.5 minutes to bind 25-hydroxyvitamin D in the sample. A 25-hydroxyvitamin D analog conjugated to bovine serum albumin and fluorescein is added along with antifluorescein-coated paramagnetic particles and allowed to react for 3.75 minutes. The reaction cuvette is washed, and acid and base reagents are added to initiate the chemiluminescent reaction. The time-to-result is 18 minutes. An inverse relationship exists between the amount of 25-hydroxyvitamin D in the patient sample and the amount of relative light units (RLUs) detected by the system.

Figure 8:
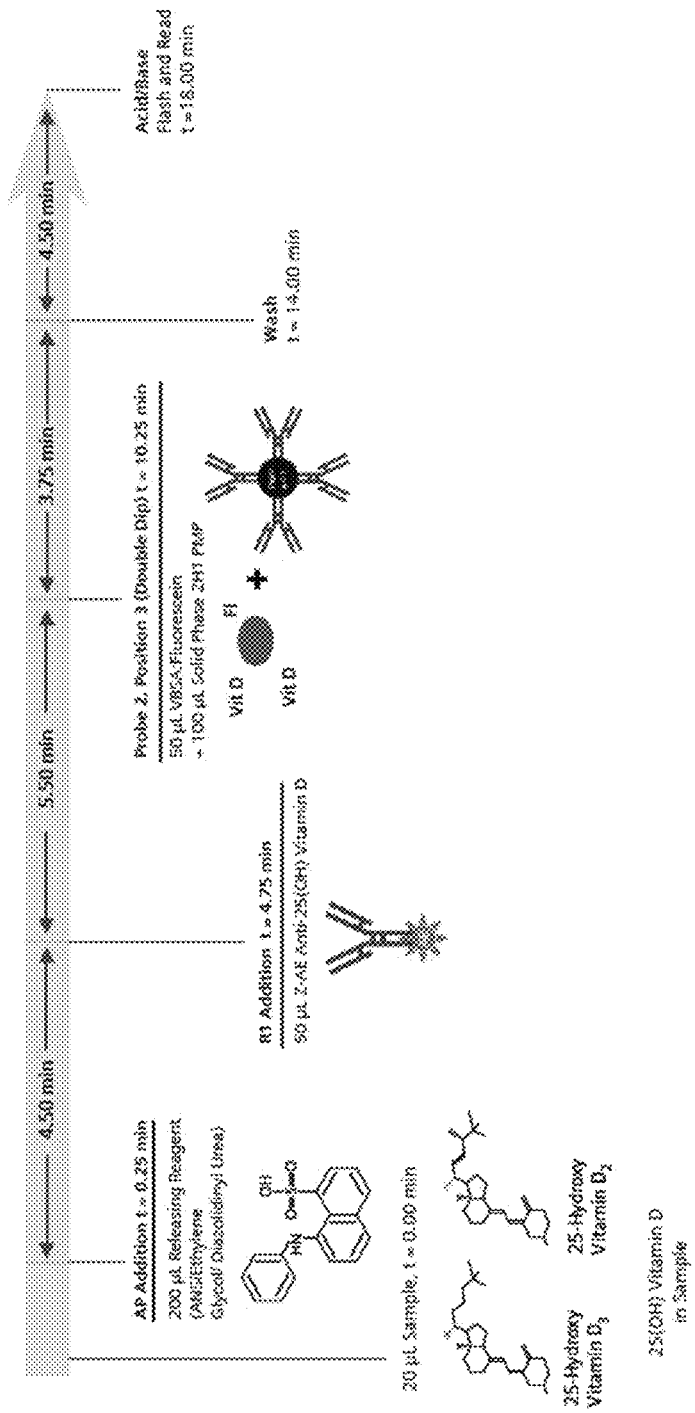
FIG. 8 shows a schematic of the ADVIA Centaur Vitamin D Total Assay. This schematic is for illustrative purposes only and should not be construed as limiting in any way.

Assay: The ADVIA Centaur Vitamin D Total assay is a one-pass, 18-minute antibody competitive immunoassay that uses an antifluorescein-labeled monoclonal antibody covalently bound to paramagnetic particles (PMPs), one monoclonal antibody labeled with acridinium ester (AE), and a vitamin D analog labeled with fluorescein (FIG. 8). The Vitamin D Total assay requires 20 µL of sample volume for a single determination. The time-to-first-result is 18 minutes and the throughput is 240 tests/hour.

Briefly, the first step of the sequential step hapten/antibody competitive immunoassay using chemiluminescent technology begins with the analyzer dispensing 20 µL of biological sample into a cuvette followed by addition of 200 µl of displacement buffer (50 mM HEPES, 150 mM NaCl, 0.09% sodium azide, pH=7.5) containing 8-anilino-1-naphthalenesulfonic acid ammonium salt (Sigma-aldrich, St. Louis, Mo.) and ethylene glycol (Sigma-aldrich, St. Louis, Mo.) and incubation for 4.5 minutes at 37° C. Lite Reagent (50 µL) containing an anti 25-hydroxy Vitamin D monoclonal antibody labeled with acridinium ester (monoclonal antibody 10H9) is added to the mixture and incubated for 5.5 min at 37° C. C22-PEG-BSA-fluorescein conjugate (50 µL) and anti-fluorescein monoclonal antibody coated paramagnetic microparticles (100 µL) are added to the mixture and incubated for 3.75 minutes at 37° C. The fourth step is separation of Solid Phase complex with bound C22-PEG-BSA-fluorescein conjugate and anti 25-hydroxy vitamin D monoclonal antibody labeled with acridinium ester, followed by washing three times to remove any free Lite Reagent. Last is the sequential dispensing of 300 µL each of acid reagent then base reagent to initiate the chemiluminescent reaction. The total incubation time from sample to result is 18 minutes. There is an indirect relationship between the amount of 25-hydroxy vitamin D present in the biological sample and the amount of chemiluminescence quantified as relative light units (RLUs). In the Centaur-based assay, there is an inverse relationship between RLUs emitted by the acridinium ester and the amount of vitamin D because the 25-hydroxyvitamin D released from the carrier protein in the plasma competes with the Vitamin D-BSA-Fluorescein for binding with a limited amount of the acridinium-labeled 10H9 monoclonal antibody. Higher levels of 25(OH)D in the patient sample would lower the amount of the acridinium-MAb-VitD-BSA-Fluorescein complex on the magnetic particles resulting in lower RLUs.

Precision: The precision study was based on the CLSI protocol EP5-A2:two runs per day for 10 days on a single ADVIA Centaur system. Assay precision was determined using samples with Vitamin D Total ranging from 4 to 120 ng/mL.

Analytical sensitivity: Analytical sensitivity is defined as the concentration that corresponds to the mean signal plus 2 SD obtained from the lowest standard, expressed in relative light units (RLUs). The analytical sensitivity study was performed following CLSI protocol EP5-A2. Analytical sensitivity was determined using 60 replicates of the lowest standard.

Limit of blank, limit of detection, and functional sensitivity: The limit of blank is defined as the concentration of analyte that corresponds to the 95th percentile of the distribution of a human negative basepool. The vitamin D total low standard was assayed 20 times using two lots of reagents on three systems (n=120). The limit of detection (LoD) is determined according to CLSI protocol EP17-A. Limit of detection is defined as the lowest concentration of vitamin D that can be detected with 95% probability. The LoD was determined by using low-level vitamin D samples that were assayed 20 times using two lots of reagents on three systems (n=120). Functional sensitivity was determined using a single instrument over 10 days. Two runs were performed per day in duplicate for a total of 60 replicates. The ADVIA Centaur Vitamin D Total sensitivity panel members concentrations ranged from 3.0 to 20.0 ng/mL. Concentrations were calculated using within-lot, day zero, two-point calibration curves.

Interference studies: Interference from endogenous and nonendongenous substances were evaluated following the guidelines in NCCLS EP-7A. Each sample was spiked with an interferent and compared to a matched unspiked control.

Cross-reactivity: Five vitamin D derivatives were analyzed using the ADVIA Centaur Vitamin D Total assay. The vitamin D derivatives were spiked into a sample containing 27 ng/mL of vitamin D total. Three replicates of the spiked samples were assayed and the vitamin D total concentration determined.

Tube type study: Correlation of EDTA and serum separator tubes (SST) tubes was analyzed using the ADVIA Centaur Vitamin D Total assay. Serum red top, SST, and EDTA tubes were collected from 119 donors and assayed using the Centaur Vitamin D Total assay. Three replicates of each sample were evaluated. Linear regression correlation between serum and SST and serum vs EDTA was determined.

Method correlation: The ADVIA Centaur Vitamin D Total assay was compared to a commercially available, FDA-cleared, Vitamin D Total immunoassay using 199 patient specimens, a single replicate for each method. Specimen concentration ranged from 5 to 150 ng/mL. In addition, 23 patient samples were assayed by LC-MS/MS and the ADVIA Centaur Vitamin D Total Assay. Specimens in this second population ranged from 11 to 82 ng/mL.

Results

The data obtained with the ADVIA Centaur Vitamin D Total assay demonstrated equimolar detection of $25(OH)D_2$ and $25(OH)D_3$ and showed traceability to LC-MS/IS. Cross-reactivity to 25(OH)D2 was determined to be 105% at 50 ng/mL. The assay demonstrated a limit of detection (LoD) of less than 3.0 ng/mL, a functional sensitivity (20% dose total CV) of less than 4 ng/mL, and an upper limit of 250 ng/mL. Total assay CVs were 6.4%, 7.1%, 4.2%, and 3.7% for samples at 22.1, 52.3, 121, and 153 ng/mL, respectively. Linearity up to 240 ng/mL was demonstrated. A correlation study against LC-MS/MS was performed with 150 serum samples, yielding a slope of 0.96, intercept of 1.0, and regression coefficient of 0.97.

Precision. The precision profile of the ADVIA Centaur Vitamin D Total assay demonstrates a total CV between 8.8% at 7.65 ng/mL to 2.0% at 123.36 ng/mL 25(OH) total vitamin D. Precision analysis is shown in Table 5.

TABLE 5

Precision analysis of ADVIA Centaur Vitamin D Total Assay

| Sample | Mean (ng/mL) | Within-Run SD (ng/mL) | Within-Run CV (%) | Total SD (ng/mL) | Total CV (%) |
|---|---|---|---|---|---|
| 1 | 7.65 | 0.65 | 8.5 | 0.67 | 8.8 |
| 2 | 10.65 | 0.85 | 8.0 | 1.07 | 10.1 |
| 3 | 13.11 | 0.84 | 6.4 | 0.91 | 6.9 |
| 4 | 15.87 | 1.02 | 6.4 | 1.18 | 7.4 |
| 5 | 18.40 | 1.31 | 7.1 | 1.44 | 7.8 |
| 6 | 22.63 | 1.79 | 7.9 | 1.79 | 7.9 |
| 7 | 59.75 | 1.76 | 3.0 | 1.92 | 3.2 |
| 8 | 99.63 | 1.95 | 2.0 | 2.07 | 2.1 |
| 9 | 112.74 | 1.98 | 1.8 | 3.07 | 2.7 |
| 10 | 115.71 | 1.98 | 1.7 | 2.55 | 2.2 |
| 11 | 123.36 | 2.29 | 1.9 | 2.51 | 2.0 |

Analytical sensitivity: The analytical sensitivity of the ADVIA Centaur Vitamin D Total assay was 2.4 ng/mL. Analytical sensitivity is shown in Table 6.

TABLE 6

Analytical sensitivity of ADVIA Centaur Vitamin D Total Assay

| Sample | Replicates | Mean RLU + 2 SD | Dose (ng/mL) |
|---|---|---|---|
| Vitamin D Blank | 60 | 688200 | 2.4 |

Figure 9:
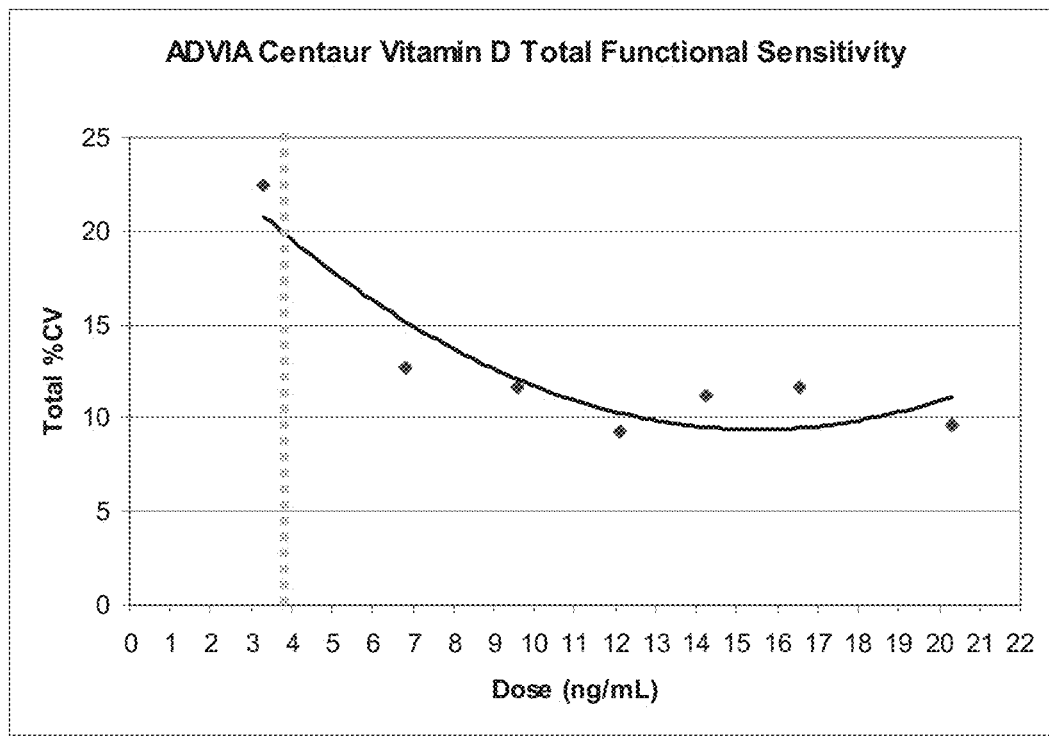
FIG. 9 shows the precision profile showing the limit of detection (LoD) and functional sensitivity (dashed line) of the ADVIA Centaur Vitamin D Total assay.

Limit of Blank, Limit of Detection, and Functional Sensitivity: The limit of blank of the ADVIA Centaur Vitamin D Total assay was 2.8 ng/mL, the limit of detection was 3.8 ng/mL, and the functional sensitivity was 4 ng/mL (FIG. 9).

Interference studies: The ADVIA Centaur Vitamin D Total assay demonstrated ≤10% bias at the concentrations tested for endogenous interferents. Results of endogenous interference studies is shown in Table 7.

TABLE 7

Interference Study Results for ADVIA Centaur Vitamin D Total Assay

| Interferent | Concentration | Vitamin D Total Expected (ng/mL) | Vitamin D Total Observed (ng/mL) | Bias (%) |
|---|---|---|---|---|
| Unconjugated Bilirubin | 60 mg/dL | 30.88 | 32.67 | 5.77 |
| Conjugated Bilirubin | 60 mg/dL | 33.82 | 30.67 | −9.31 |
| Albumin | 9 g/dL | 22.5 | 20.4 | −9.33 |
| Hemoglobin | 500 mg/dL | 29.08 | 29.70 | 2.13 |
| Triglycerides | 500 mg/dL | 22.7 | 23.6 | 3.96 |
| Uric Acid | 20 mg/dL | 35.45 | 33.45 | −5.64 |

Cross-reactivity: The ADVIA Centaur Vitamin D Total assay demonstrated very low cross-reactivity to the nonhydroxylated forms of vitamin D2 and vitamin D3, and to 3-epi-25(OH)D3. Cross-reactivity analysis results are shown in Table 8.

TABLE 8

Cross-reactivity of ADVIA Centaur Vitamin D Total Assay

| Crossreactant | Concentration (ng/mL) | Expected (Endogenous) Vitamin D Total (ng/mL) | Observed Vitamin D Total (ng/mL) | Cross-reactivity (%) |
|---|---|---|---|---|
| 25-(OH)-Vit D3 | 27 | 0 | 27 | 100 |
| 25-(OH)-Vit D2 | 30 | 27 | 58 | 102 |
| Vitamin D2 | 100 | 27 | 28 | 0.04 |
| Vitamin D3 | 100 | 27 | 28 | 0.04 |
| 3-epi-25(OH)D3 | 100 | 27 | 27 | 0.0 |

Figure 10:
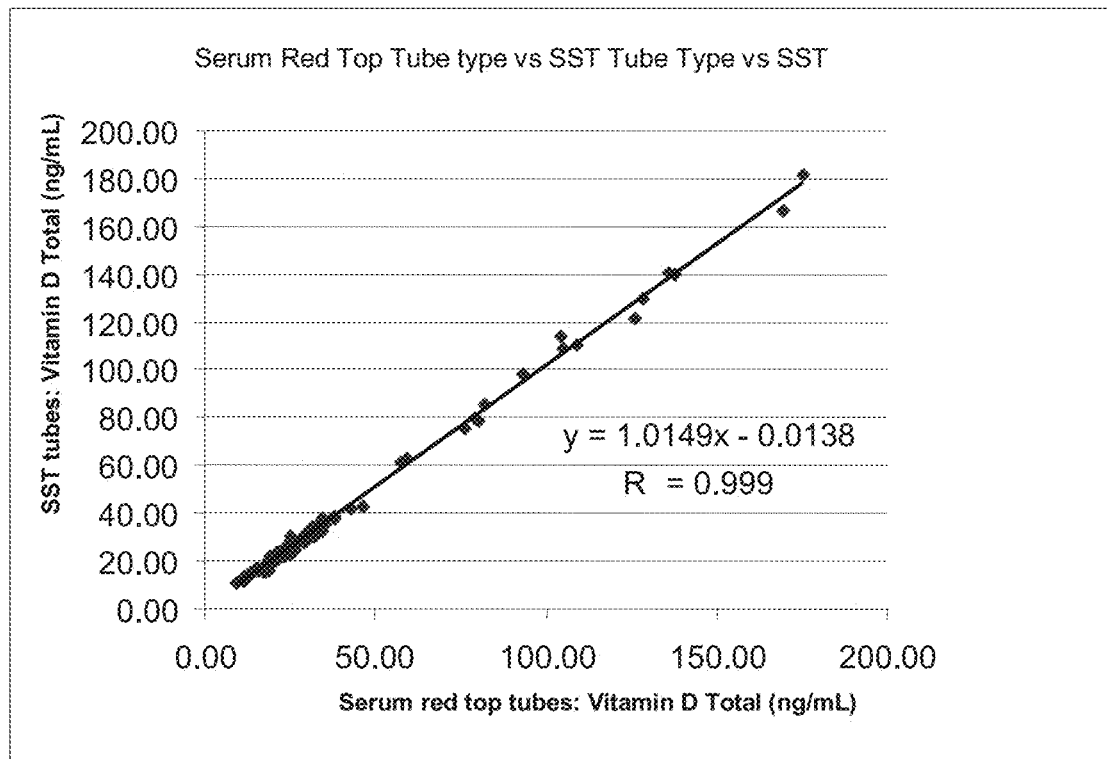
FIG. 10 shows the correlation of Vitamin D Total levels collected from 119 donors in serum red top and SST tubes and functional sensitivity.
Figure 11:
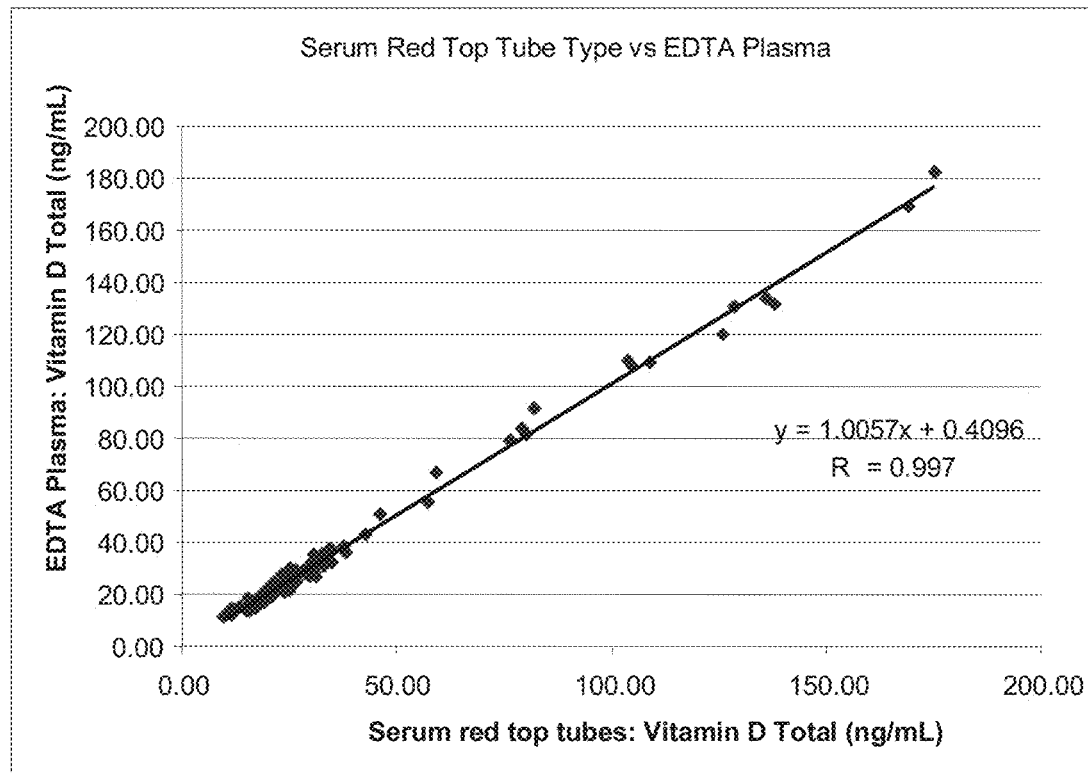
FIG. 11 shows the correlation of Vitamin D Total levels collected from 119 donors in serum red top and EDTA tubes.

Tube type study: A sample tube type correlation was performed with 119 donor specimens collected in serum red top, SST, and EDTA tube types. Regression analysis between serum red top and SST demonstrates a correlation coefficient (R) of 0.999, aslope of 1.01, and an intercept of −0.14 (FIG. 10). Regression analysis between serum red top and EDTA demonstrates a correlation coefficient (R) of 0.997, a slope of 1.00, and an intercept of 0.41 (FIG. 11).

Figure 12:
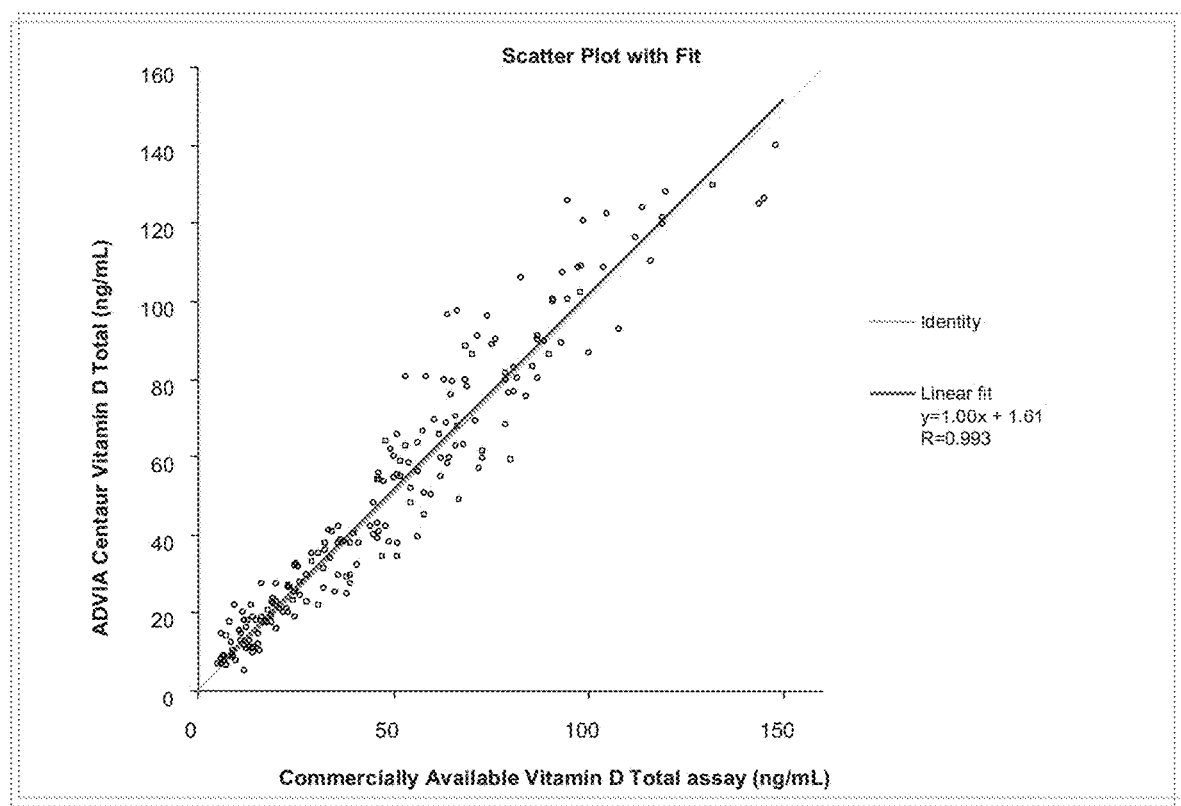
FIG. 12 shows the correlation of the ADVIA Centaur and a commercially available Vitamin D Total assay.
Figure 13:
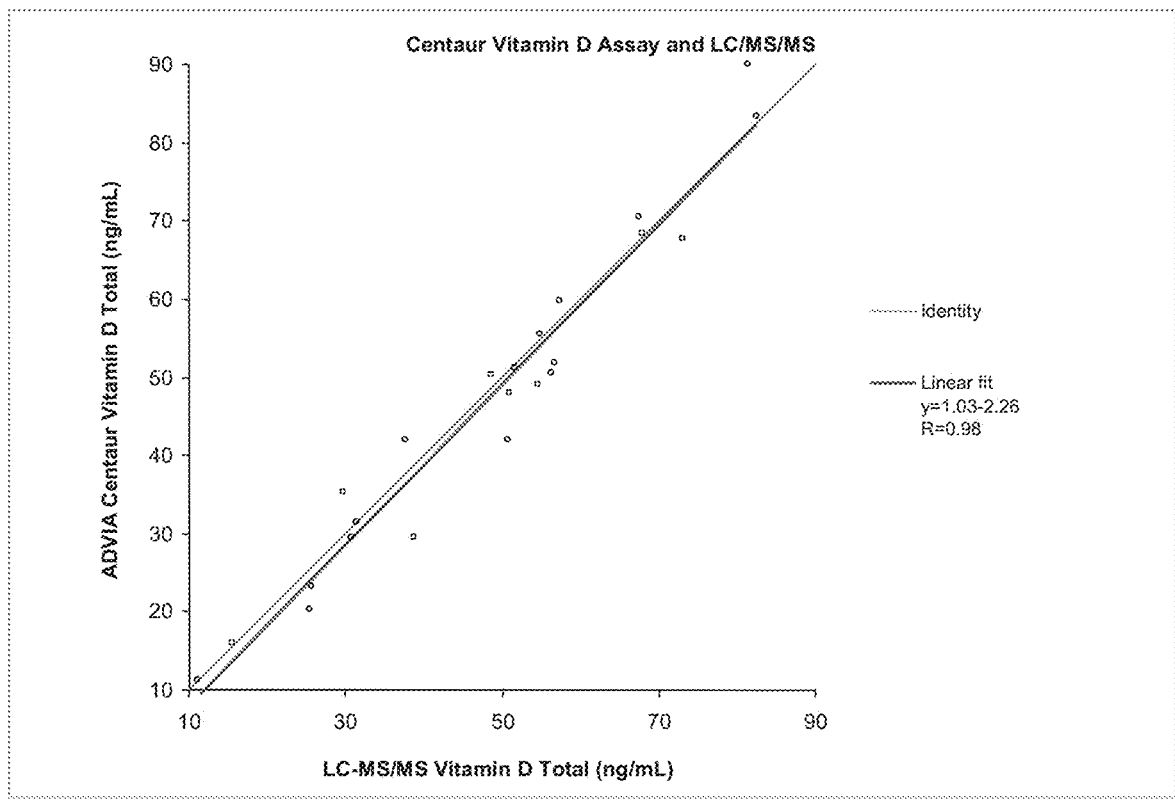
FIG. 13 shows the correlation of the ADVIA Centaur and LC-MS/MS Vitamin D Total assays.

Method comparison: A sample correlation was performed with 199 specimens comparing the ADVIA Centaur Vitamin D Total assay to a commercially available, FDA-cleared, Vitamin D Total assay. Regression analysis demonstrated a correlation coefficient (R) of 0.993, a slope of 1.00, and an intercept of 1.61 (FIG. 12). In, addition 23 specimens were assayed comparing the ADVIA Centaur Vitamin D Total assay to a commercially available Vitamin D Total LC-MS/MS assay. Regression analysis demonstrated a correlation coefficient (R) of 0.98, a slope of 1.03, and an intercept of −2.3 (FIG. 13).

| SEQ ID NO. | Sequence |
|---|---|
| 1 | TTTTGGGGCCAAGGCACCACTCTCACAGTCTCCTCG |
| 2 | TACACCATGAACTGGGTGAAGCAGAGCCATGGAAAGAAC |
| 3 | TTTACTATCTATAATCAGAAG |
| 4 | ATAAGAGCGCATTACGACGGGAGAGTT |
| 5 | GTGCAGCTGCTCGAGTCTGGACCTGAGCTGGTGAAGCCT GGAGCTTCAATGAAGATATCCTGCAAGGCTTCTGGTTAC TCATTCACTGAC |
| 6 | CTTGAGTGGATTGGACTTATTAATCCTTACAATGGT |
| 7 | TTCAAGGGCAAGGCCACATTAACTGTAGACAAGTCATCC AGCACAGCCTACATGGAACTCCTCAGTCTGACATCTGAA GACTCTGCAGTCTATTACTTT |
| 8 | GTGCAGCTGCTCGAGTCTGGACCTGAGCTGGTGAAGCCT GGAGCTTCAATGAAGATATCCTGCAAGGCTTCTGGTTAC TCATTCACTGACTACACCATGAACTGGGTGAAGCAGAGC CATGGAAAGAACCTTGAGTGGATTGGACTTATTAATCCT TACAATGGTTTTACTATCTATAATCAGAAGTTCAAGGGC AAGGCCACATTAACTGTAGACAAGTCATCCAGCACAGCC TACATGGAACTCCTCAGTCTGACATCTGAAGACTCTGCA GTCTATTACTTTATAAGAGCGCATTACGACGGGAGAGTT TTTTGGGGCCAAGGCACCACTCTCACAGTCTCCTCG |
| 9 | FWGQGTTLTVSS |
| 10 | YTMNWVKQSHGKN |
| 11 | FTIYNQK |
| 12 | IRAHYDGRV |
| 13 | VQLLESGPELVKPGASMKISCKASGYSFTD |
| 14 | LEWIGLINPYNG |
| 15 | FKGKATLTVDKSSSTAYMELLSLTSEDSAVYYF |
| 16 | VQLLESGPELVKPGASMKISCKASGYSFTDYTMNWVKQSHGKNLE WIGLINPYNGFTIYNQKFKGKATLTVDKSSSTAYMELLSLTSEDS AVYYFIRAHYDGRVFWGQGTTLTVSS |
| 17 | ACGTTCGGAGGGGGACCAAGCTAGAAATAAAACGG |
| 18 | CAGAGCCTTGTACACAGTAATGGAAACACCTATTTACAT |
| 19 | CTGATCTACCAAGTTTCCAAC |
| 20 | TGCTCTCAAATTACACATTTTCCTCCC |
| 21 | TGTGAACTAGTGATGACCCAGTCTCCACTCTCCCTGCCTGTCAGT CTTGGAGATCAAGCCTCCGTCTCTTGCAGATCTAGT |
| 22 | CGGTACCTGCAGAAGCCAGGCCAGTCTCCAAAGCTC |
| 23 | CGATTTTCTGGGGTCCCAGACAGGTTCAGTGGCAGTGGATCAGG GACAGATTTCACACTCAAGATCACCAGAGTGGAGGCTGAGGATC TGGGAGTTTATTTC |
| 24 | TGTGAACTAGTGATGACCCAGTCTCCACTCTCCCTGCCTGTCAGT CTTGGAGATCAAGCCTCCGTCTCTTGCAGATCTAGTCAGAGCCTT |

| SEQ ID NO. | Sequence |
|---|---|
| | GTACACAGTAATGGAAACACCTATTTACATCGGTACCTGCAGAA GCCAGGCCAGTCTCCAAAGCTCCTGATCTACCAAGTTTCCAACCG ATTTTCTGGGGTCCCAGACAGGTTCAGTGGCAGTGGATCAGGGA CAGATTTCACACTCAAGATCACCAGAGTGGAGGCTGAGGATCTG GGAGTTTATTTCTGCTCTCAAATTACACATTTTCCTCCCACGTTC GGAGGGGGGACCAAGCTAGAAATAAAACGG |
| 25 | TFGGGTKLEIKR |
| 26 | QSLVHSNGNTYLH |
| 27 | LIYQVSN |
| 28 | CSQITHFPP |
| 29 | CELVMTQSPLSLPVSLGDQASVSCRSS |
| 30 | RYLQKPGQSPKL |
| 31 | RFSGVPDRFSGSGSGTDFTLKITRVEAEDLGVYF |
| 32 | CELVMTQSPLSLPVSLGDQASVSCRSSQSLVHSNGNTYLHRYLQKP GQSPKLLIYQVSNRFSGVPDRFSGSGSGTDFTLKITRVEAEDLGVY FCSQITHFPPTFGGGTKLEIKR |

What is claimed:

1. A cell that produces a monoclonal antibody, or an antigen-binding fragment thereof, that binds 25-hydroxyvitamin D2 and 25-hydroxyvitamin D3, wherein the monoclonal antibody comprises:
   a heavy chain variable domain comprising the amino acid sequence of SEQ ID NO: 16; and
   a light chain variable domain comprising the amino acid sequence of SEQ ID NO: 32.

2. A kit comprising a monoclonal antibody, or an antigen-binding fragment thereof, that binds 25-hydroxyvitamin D2 and 25-hydroxyvitamin D3, wherein the monoclonal antibody comprises:
   a heavy chain variable domain comprising the amino acid sequence of SEQ ID NO: 16; and
   a light chain variable domain comprising the amino acid sequence of SEQ ID NO: 32.

3. The kit of claim 2 further comprising an alkaline phosphatase-conjugated vitamin D-C22-bovine serum albumin (BSA).

4. The cell of claim 1, wherein the antibody is a murine antibody.

5. The cell of claim 1, wherein the cell is a hybridoma cell.

6. The cell of claim 1, wherein the cell is recombinantly produced.

7. The cell of claim 1, wherein the cell comprises an isolated polynucleotide encoding the amino acid sequence of SEQ ID NO: 16 and the amino acid sequence of SEQ ID NO: 32.

8. The cell of claim 7, wherein the isolated polynucleotide comprises SEQ ID NO: 8 and SEQ ID NO: 24.

9. The cell of claim 7, wherein the isolated polynucleotide is recombinant.

10. The cell of claim 7, wherein the isolated polynucleotide is a cDNA.

* * * * *